United States Patent
Lau et al.

(10) Patent No.: US 10,512,429 B2
(45) Date of Patent: Dec. 24, 2019

(54) DISCRIMINATION OF CHEYNE-STOKES BREATHING PATTERNS BY USE OF OXIMETRY SIGNALS

(71) Applicant: ResMed Limited, Bella Vista (AU)

(72) Inventors: Chun Yui Lau, Wollstonecraft (AU); Jeffrey Peter Armitstead, Sydney (AU)

(73) Assignee: ResMed Pty Ltd (AU)

( * ) Notice: Subject to any disclaimer, the term of this patent is extended or adjusted under 35 U.S.C. 154(b) by 834 days.

(21) Appl. No.: 14/757,601

(22) Filed: Dec. 23, 2015

(65) Prior Publication Data
US 2016/0120464 A1    May 5, 2016

Related U.S. Application Data

(63) Continuation-in-part of application No. 13/252,640, filed on Oct. 4, 2011, which is a continuation of
(Continued)

(51) Int. Cl.
*A61B 5/1455*   (2006.01)
*A61B 5/08*     (2006.01)
(Continued)

(52) U.S. Cl.
CPC ........... *A61B 5/4818* (2013.01); *A61B 5/087* (2013.01); *A61B 5/0826* (2013.01);
(Continued)

(58) Field of Classification Search
CPC ........... A61B 5/14551; A61B 5/14542; A61B 5/0826; A61B 5/4818
See application file for complete search history.

(56) References Cited

U.S. PATENT DOCUMENTS

| 4,365,636 A | 12/1982 | Barker |
| 4,765,340 A | 8/1988 | Sakai et al. |

(Continued)

FOREIGN PATENT DOCUMENTS

| CN | 1241394 A | 1/2000 |
| CN | 101087559 A | 12/2007 |

(Continued)

OTHER PUBLICATIONS

International Search Report and Written Opinion, PCT/AU2010/000416, dated Aug. 5, 2010.
(Continued)

*Primary Examiner* — Meredith Weare
(74) *Attorney, Agent, or Firm* — Botos Churchill IP Law LLP

(57) ABSTRACT

Methods and apparatus provide Cheyne-Stokes respiration ("CSR") detection based on a blood gas measurements such as oximetry. In some embodiments, a duration, such as a mean duration of contiguous periods of changing saturation or re-saturation occurring in an epoch taken from a processed oximetry signal, is determined. An occurrence of CSR may be detected from a comparison of the duration and a threshold derived to differentiate saturation changes due to CSR respiration and saturation changes due to obstructive sleep apnea. The threshold may be a discriminant function derived as a classifier by an automated training method. The discriminant function may be further implemented to characterize the epoch for CSR based on a frequency analysis of the oximetry data. Distance from the discriminant function may be utilized to generate probability values for the CSR detection.

25 Claims, 27 Drawing Sheets

Related U.S. Application Data application No. 11/576,210, filed as application No. PCT/AU2005/001942 on Dec. 21, 2005, now Pat. No. 8,066,647, application No. 14/757,601, which is a continuation of application No. 13/256,649, filed as application No. PCT/AU2010/000416 on Apr. 15, 2010, now abandoned.

(60) Provisional application No. 61/170,734, filed on Apr. 20, 2009, provisional application No. 60/638,169, filed on Dec. 23, 2004.

(51) Int. Cl.

| A61B 5/00 | (2006.01) |
|---|---|
| A61B 5/087 | (2006.01) |
| G06K 9/00 | (2006.01) |
| G06K 9/62 | (2006.01) |
| A61M 16/00 | (2006.01) |

(52) U.S. Cl.
CPC ........ *A61B 5/14551* (2013.01); *A61B 5/7267* (2013.01); *A61B 5/7278* (2013.01); *G06K 9/0053* (2013.01); *G06K 9/6262* (2013.01); *G06K 9/6269* (2013.01); *A61B 5/6819* (2013.01); *A61B 5/6823* (2013.01); *A61B 5/726* (2013.01); *A61B 5/7207* (2013.01); *A61B 5/7221* (2013.01); *A61B 5/7232* (2013.01); *A61M 16/00* (2013.01); *A61M 2230/40* (2013.01)

(56) References Cited

U.S. PATENT DOCUMENTS

| 4,941,474 A * | 7/1990 | Pratt, Jr. ............... A61B 8/0875 |
|---|---|---|
| | | 600/437 |
| 5,078,136 A | 1/1992 | Stone et al. |
| 5,203,343 A | 4/1993 | Axe et al. |
| 5,218,962 A * | 6/1993 | Mannheimer ...... A61B 5/14542 |
| | | 356/41 |
| 5,385,144 A | 1/1995 | Yamanishi et al. |
| 5,575,285 A | 11/1996 | Takanashi et al. |
| 5,660,183 A * | 8/1997 | Chiang ................ A61N 1/3702 |
| | | 600/508 |
| 5,745,601 A | 4/1998 | Lee et al. |
| 5,794,623 A | 8/1998 | Forbes |
| 5,947,908 A | 9/1999 | Morris |
| 6,138,675 A | 10/2000 | Berthon-Jones |
| 6,171,258 B1 | 1/2001 | Karakasoglu et al. |
| 6,223,064 B1 * | 4/2001 | Lynn .................. A61B 5/14551 |
| | | 600/324 |
| 6,290,654 B1 | 9/2001 | Karakasoglu |
| 6,454,719 B1 | 9/2002 | Greenhut |
| 6,532,959 B1 | 3/2003 | Berthon-Jones |
| 6,752,151 B2 | 6/2004 | Hill |
| 6,760,608 B2 | 7/2004 | Lynn |
| 6,811,538 B2 | 11/2004 | Westbrook et al. |
| 6,830,548 B2 | 12/2004 | Bonnet et al. |
| 6,839,581 B1 * | 1/2005 | El-Solh ................. A61B 5/145 |
| | | 600/323 |
| 7,081,095 B2 | 7/2006 | Lynn et al. |
| 7,309,314 B2 | 12/2007 | Grant et al. |
| 7,381,185 B2 | 6/2008 | Zhirnov et al. |
| 7,398,115 B2 | 7/2008 | Lynn |
| 7,717,110 B2 | 5/2010 | Kane et al. |
| 7,803,119 B2 | 9/2010 | Reisfeld |
| 8,046,040 B2 | 10/2011 | Ali et al. |
| 8,066,647 B2 | 11/2011 | Armitstead |
| 8,750,953 B2 | 6/2014 | Ochs et al. |
| 2001/0018557 A1 | 8/2001 | Lynn et al. |
| 2002/0002327 A1 | 1/2002 | Grant et al. |
| 2002/0035315 A1 | 3/2002 | Ali et al. |
| 2002/0088465 A1 | 7/2002 | Hill |
| 2002/0095076 A1 | 7/2002 | Krausman et al. |
| 2002/0148466 A1 | 10/2002 | Berthon-Jones |
| 2003/0033094 A1 | 2/2003 | Huang |
| 2003/0187638 A1 | 10/2003 | Causevic et al. |
| 2003/0199945 A1 | 10/2003 | Ciulla |
| 2003/0233048 A1 | 12/2003 | Silverman et al. |
| 2004/0030231 A1 * | 2/2004 | Norris ................ A61B 5/14551 |
| | | 600/323 |
| 2004/0071337 A1 | 4/2004 | Jeung et al. |
| 2004/0134496 A1 | 7/2004 | Cho et al. |
| 2004/0254482 A1 | 12/2004 | Anderson et al. |
| 2005/0033128 A1 * | 2/2005 | Ali ....................... A61B 5/1455 |
| | | 600/323 |
| 2005/0055276 A1 | 3/2005 | Kiani et al. |
| 2005/0065417 A1 * | 3/2005 | Ali ....................... A61B 5/0002 |
| | | 600/323 |
| 2005/0115561 A1 | 6/2005 | Stahmann et al. |
| 2005/0256420 A1 | 11/2005 | Norman et al. |
| 2005/0267362 A1 | 12/2005 | Mietus et al. |
| 2006/0030764 A1 * | 2/2006 | Porges ............... A61B 5/14551 |
| | | 600/323 |
| 2006/0195025 A1 | 8/2006 | Ali et al. |
| 2006/0258921 A1 | 11/2006 | Addison et al. |
| 2007/0213621 A1 | 9/2007 | Reisfeld et al. |
| 2007/0213624 A1 | 9/2007 | Reisfeld et al. |
| 2008/0177195 A1 | 7/2008 | Armitstead |
| 2009/0069649 A1 * | 3/2009 | Budiman ........... A61B 5/14532 |
| | | 600/309 |
| 2009/0209839 A1 * | 8/2009 | Ochs .................. A61B 5/14551 |
| | | 600/364 |
| 2009/0240119 A1 | 9/2009 | Schwaibold et al. |
| 2009/0281435 A1 * | 11/2009 | Ahmed .............. A61B 5/02416 |
| | | 600/502 |
| 2009/0292215 A1 | 11/2009 | Todros |
| 2010/0081906 A1 | 4/2010 | Hayter et al. |

FOREIGN PATENT DOCUMENTS

| EP | 1295623 A1 | 3/2003 |
|---|---|---|
| JP | 2001-037739 A | 2/2001 |
| JP | 2001-037742 A | 2/2001 |
| JP | 2002-153432 A | 5/2002 |
| JP | 2002-516159 A | 6/2002 |
| JP | 2003-290154 A | 10/2003 |
| JP | 2003-532456 A | 11/2003 |
| JP | 2004-512066 A | 4/2004 |
| JP | 2004-514491 A | 5/2004 |
| JP | 2004-526470 A | 9/2004 |
| JP | 2008-525060 A | 7/2008 |
| WO | 00/19895 A1 | 4/2000 |
| WO | 00/20047 A2 | 4/2000 |
| WO | 01064101 A1 | 9/2001 |
| WO | 01/76459 A2 | 10/2001 |
| WO | 02/26283 A2 | 4/2002 |
| WO | 0243579 A2 | 6/2002 |
| WO | 03030804 A2 | 4/2003 |
| WO | 03/057025 A2 | 7/2003 |
| WO | 2004/047618 A2 | 6/2004 |
| WO | 2004/062485 A2 | 7/2004 |
| WO | 2004075746 A2 | 9/2004 |
| WO | 2005/112760 A1 | 12/2005 |
| WO | 2006066337 A1 | 6/2006 |
| WO | 2007115553 A1 | 10/2007 |
| WO | 2008/154430 A2 | 12/2008 |
| WO | 2009/118737 A2 | 10/2009 |

OTHER PUBLICATIONS

Platt, J. (2000). Probablistic outputs for support vector machines and comparison to regularized likelihood methods. In A. Smola, P. Bartlett, Schölkopf, & D. Schuurmans (Eds.), Advances in large margin classifiers, Cambridge: MIT Press.
Staniforth, A.D., et al., "Nocturnal Desaturation in Patients with Stable Heart Failure," Heart 1998 79:394-399.
Javaheri et al., Circulation 1998, 97:2154-2159.
Sin et al., Am J Respir Crit Care Med, 1999; 160:1101-1106.
Eckert et al., Chest, 2007, 131:595-607.

(56) References Cited

OTHER PUBLICATIONS

Leite et al., "Periodic Breathing During Incremental Exercise Predicts Mortality in Patients with Chronic Heart Failure Evaluated for Cardiac Transplantation", 2003, Journal of the American College of Cardiology, vol. 41, 2175.
Extended Search Report, European Patent Office, Application No. 10150057.7, Feb. 26, 2010.
Loube et al (1999). "Comparison of Respiratory Polysomnographic Parameters in Matched Cohorts of Upper Airway Resistance and Obstructive Sleep Apnea Syndrome Patients", Chest: 115; pp. 1519-1524.
Parra et al (2000), "Time Course of Sleep-related Breathing Disourders in First-Ever Stroke or Transient Ischemic Attack", American Journal Respiratory & Critical Care Medicine; 161; pp. 375-380.
Willson et al, (2001). "Noninvasive Pressure Present Ventilation for the Treatment of Cheyne-Stokes Respiration During Sleep". European Respiratory Journal; 17; pp. 1250-1257.
Kohnlein et al., (2002), "Assisted Ventilation for Heart Failure Patients with Cheyne-Stokes Respiration", European Respiratory Journal; 20; pp. 934-941.
Brack, Thomas, (2003), "Cheyne-Stokes Respiration in Patients with Congestive Heart Failure", Swiss Medical Weekly; 133; pp. 605-610.
Ryan et al., (2005), "Periodicity of Obstructive SLeep APnea in Patients with and without Heart Failure", Chest; 127; pp. 536-542.
Hori et al., (2001), "Proposed Supplements and Amendments to 'A Manual of Standardized Terminology and Techniques and Scoring System for Sleep Stages of Human Subjects', the Rechtschaften & Kales (1968) Standard", Psychiatry and ClinicalNeurosciences; 55; pp. 305-310.
Shochat et al., (2002), "The SleepStrip TM: an Apnoea Screener for the Early Detection of Sleep Apnea Syndrome", European Respiratory Journal; 19; pp. 121-126.
Examination Report, New Zealand Application No. 593988, New Zealand Patent Office, Jul. 15, 2011.
Chinese Office Action for corresponding application No. 200580044321.0; Aug. 22, 2008.
Chinese Office Action for corresponding application No. 200580044321.0; Aug. 7, 2009.
Chinese Office Action for corresponding application No. 200580044321.0; Jan. 22, 2010.
Chinese Office Action for corresponding application No. 200580044321.0; Apr. 29, 2010.
Sullivan CE et al.: 'Reversal of obstructive sleep apnea by continuous positive airway pressure applied through the nares' Lancet vol. 1, No. 8225, Apr. 18, 1981, pp. 862-5.
Teschler H et al.: 'Adaptive pressure support servo-ventilation: a novel treatment for Cheyne-Stokes respiration in heart failure' AIN J Respir Crit Care Med. vol. 164, No. 4, Aug. 15, 2001, pp. 614-9.
International Search Report for Application No. PCT/AU2005/001942 dated Mar. 29, 2006.
Chinese Office Action for corresponding Application No. 201080025272.7 dated Mar. 12, 2014.
Poets et al. "Detection of Movement Artifact in Recorded Pulse Oximeter Saturation." Eur J Pediatr. Oct. 1997;156 (10):808-11.
Chinese Office Action for corresponding Application No. CN201110064713.0 dated Feb. 26, 2014.
European Communication issued in corresponding EP application No. 10766483.1 dated Sep. 19, 2016.
El-Solh, A. , et al., "The utility of neural network in the diagnosis of Cheyne-Stokes respiration", Journal of Medical Engineering & Technology Taylor & Francis UK, vol. 27, No. 2, XP008181361, pp. 54-58, Apr. 2003 (Apr. 2003).
Series, Frederic , et al., "Prospective Evaluation o f Nocturnal Oximetry for Detection of Sleep-Related Breathing Disturbances in Patients With Chronic Heart Failure", CHEST vol. 127, No. 5, XP055297864, US, pp, 1507-1514, May 1, 2005 (May 1, 2005).

\* cited by examiner

FIG. 16: Log (max-jump feature)

FIG. 17: Epoch primary features

FIG. 18: Feature Calculation

C=Cheyne-Stokes
O=Obstructive Sleep Apnea
M=Mixed Cheyne-Stokes and Obstructive Sleep Apnea CS=Cheyne-Stokes
OSA=Obstructive Sleep Apnea
MIX=Mixed Cheyne-Stokes and Obstructive Sleep Apnea

DISCRIMINATION OF CHEYNE-STOKES BREATHING PATTERNS BY USE OF OXIMETRY SIGNALS

CROSS-REFERENCE TO RELATED APPLICATIONS

The present application claims priority to U.S. patent application Ser. No. 13/259,649, filed Sep. 23, 2011, which is a national phase entry under 35 U.S.C. § 371 of International Application No. PCT/AU2010/000416 filed Apr. 15, 2010, published in English which claims priority from U.S. Provisional Patent Application No. 61/170,734, filed Apr. 20, 2009, and the present application is a continuation-in-part and claims priority to co-pending U.S. patent application Ser. No. 13/252,640, filed Oct. 4, 2011, which is a continuation of U.S. patent application Ser. No. 11/576,210, filed Mar. 28, 2007, which is a national stage of PCT/AU2005/001942 filed Dec. 21, 2005, which claims priority to U.S. Provisional Patent Application No. 60/638,169 filed on Dec. 23, 2004, all of which are incorporated herein by reference.

FIELD OF THE TECHNOLOGY

This technology relates to the discrimination of breathing abnormalities by applying quantitative measures to a physiological signal for use as a clinical decision-support tool. In particular it relates to the discrimination of Cheyne-Stokes Respiration ("CSR") by the analysis of oximetry signals, which may optionally be in conjunction with flow signals. The technology may also relate to algorithms and diagnostic apparatus for the detection of sleep disordered breathing patterns and the discrimination between patterns of different disease states such as obstructive sleep apnea, central sleep apnea and Cheyne-Stokes breathing and mixed sleep apnea. The technology may also relate to the training of a classifier able to provide probability values for CSR discrimination. The technology may also relate to techniques for improving the readout of oximetry signals by removing artifacts recognizable in the context of CSR.

BACKGROUND OF THE TECHNOLOGY

Breathing Disorders

Sleep-disordered breathing (SDB) encompasses a group of disorders where the breathing pattern or quality of ventilation is abnormal during sleep. Obstructive sleep apnea (OSA), the most common such disorder (effecting possible 4-5% of the adult population), is characterized by repetitive closing or collapse of the upper airway and partial or complete diminution of breathing. The obstruction is normally ended by the patient arousing briefly when the muscles of the upper airway act to clear the obstruction. During the repetitive cycle of obstruction and arousal, the OSA patient will always continue to make "efforts" to breath; in other words there is no central or brain-mediated disruption to the breathing cycle.

Conversely, in central sleep apnea (CSA), there is a disruption to breathing which is brain or control-centre in origin. Cheyne-Stokes breathing (CSB) is one of the more common forms of CSA. It is caused by an abnormal limit-cycle instability of the patient's respiratory controller in which there are rhythmic alternating periods of waxing and waning ventilation. Patients with cardiac failure (a condition where the heart fails to pump adequately) often have CSA, especially as the condition deteriorates or where therapy has ceased to allow effective compensation by the heart. Cheyne-Stokes breathing appears as a cyclical variation in tidal volume seen in heart failure patients. The cycle consists of an apnoea or hypopnoea followed by an overshooting hyperpnoea which often (but not always) has a characteristic hump backed morphology s a.k.a. a "Sydney Harbor Bridge" shape. The exact cause of CS breathing is not fully understood. However, the characteristic waxing and waning cycle is strongly reminiscent of limit cycles in a poorly adjusted control system with a maladjusted gain or destabilizing feedback-loop delay.

Sleep-disordered breathing is undesirable in all its forms because it disrupts sleep architecture (the pattern and proportion of the different forms of sleep) leading to daytime somnolence. The repetitive cessation or diminution of ventilation causes (sometimes dramatic) drops in blood oxygenation levels. These and other complications are probably responsible for the now established sequelae of cardiovascular conditions.

The treatment of choice for OSA is continuous positive airway pressure (CPAP) as first described by Sullivan [Sullivan C E, et al. Reversal of obstructive sleep apnea by continuous positive airway pressure applied through the nares. Lancet 1981 Apr. 18; 1(8225):862-5]. CPAP is also used to treat some heart-failure patients with CSA and congestive heart failure (fluid on the lungs). However, Cheyne-Stokes breathing is ineffectively treated by CPAP and may require the application of servo-ventilation [Teschler H et al. Adaptive pressure support servo-ventilation: a novel treatment for Cheyne-Stokes respiration in heart failure. Am J Respir Crit Care Med. 2001 Aug. 15; 164(4):614-9. Berthon-Jones Ventilatory assistance for treatment of cardiac failure and Cheyne-Stokes breathing. U.S. Pat. No. 6,532,959].

Diagnosis From Multiple Signals

The gold standard for the diagnosis of SDB and sleep apnea is the polysomnograph (PSG): the measurement and recording of a multitude of physiological signals during a stay overnight in a sleep laboratory. Briefly, the PSG signal ensemble normally includes one or more signals indicative of a respiratory parameters such as patient airflow rate (for the calculation of ventilation and the detection of apneas and hypopnoeas), multiple electroencephalogram (EEG), electrooculogram (EOG) and electromyogram (EMG) signals (for the determination of patient sleep state, position and the detection of arousals from sleep), breathing effort signals (either chest and abdominal distension bands or an esophageal pressure-measuring catheter), snore amplitude, and oxygen saturation. Another method of diagnosing SDB is polygraphy (PG) whereby a reduced number of parameters are recorded while the patient sleeps. These parameters include: nasal/oral airflow rate, snore amplitude, oxygen saturation, respiratory effort (thoracic and abdominal) and body position.

In both the PSG and the PG a breathing-effort signal is recorded to enable the discrimination of OSA events from CSA or Cheyne-Stokes breathing. (A third type of event is also possible—the mixed apnea—where the event is initiated by a centrally-mediated lack of breathing drive and ends with an airway obstruction and subsequent arousal). It is impossible for the inexperienced observer to reliably determine the type of apnea without reference to at least the flow signal and a measure of breathing effort. However, an experienced and trained observer (expert) can often readily detect patterns in a run of events (apneas/hypopnoeas) allowing a reliable determination of the type of underlying disease. This is especially true of Cheyne-Stokes breathing which has a very characteristic waxing and waning pattern of ventilation.

Simple Recording Devices

The performance of either a PSG or PG requires trained technicians, is expensive, is time consuming and can itself introduce sleep disturbances. Also, it is well known that a shortage of sleep laboratories is hampering the diagnosis and treatment of current SDB patients, let alone what is considered a vast undiagnosed population. For these reasons a type of "screening" device (e.g., the microMesan® from MAP of Germany, or the ApneaLink™ from ResMed) is available to test patients suspected of having sleep-disordered breathing. Such devices are small, recording just one or two physiological signals, and can be readily sent home with the patient for a screening study. For example: patients' nasal airflow can be recorded and later examined by a physician using a personal computer and a connection to the device. A software package would then be available to read the data from the device, show statistics and make recommendations regarding suspected sleep-related pathology.

Diagnosis Classifier

The calculation of the apnea-hypopnoea index (AHI, number of such events per hour on average) is a measure regularly used to guide the direction of either treatment or further investigation with a full PSG or PG. A computer program or algorithm which further enables the discrimination between different underlying disease states based on the recorded breathing patterns provides added guidance to the clinical pathway. A strong indication of Cheyne-Stokes disease, for example, would suggest completely different follow-up compared to the more common forms of sleep apnea.

The concept of a classifier is common to many fields where it is desirable to assign an object or an underlying state of an object to one of a number of classes. This concept is used, for example, in the fields of voice recognition (where sound bytes are classified as different words or syllables), radar detection (where visual signals are classified as enemy/friendly targets) and medical diagnosis (where test results are used to classify a patient's disease state). The design of a classifier falls under the field of Pattern Recognition and a classifier can be of the supervised type (the classifier is built from training data which has been pre-classed by a supervisor or "expert") or unsupervised type (where the natural ordering or clustering of the data determines the different classes). Time signal classification usually relies on representing the signal at particular time points with "features". Features are simply numbers that distill the essence of the signal at a point in time, a form of compression. A set (or vector) of features is called a "pattern". A classifier takes a pattern and manipulates it mathematically with a suitable algorithm to produce a probability value for each of a number of classes. The pattern is assigned to the class with the highest probability.

In U.S. Pat. No. 6,839,581 there is disclosed a method for detecting CS respiration in patients with congestive heart failure by performing spectral analysis of overnight oximeter recordings to obtain a set of parameters that can be used in the construction of a classification tree and a trained neural network.

In summary, sleep-disordered breathing is a common syndrome with different underlying disease types requiring very different treatment options. There is a need for a small and relatively inexpensive screening devices that can help unblock the treatment bottleneck that currently exists at the sleep laboratory. An algorithm and diagnostic apparatus that can replicate the expert's ability to detect breathing patterns associated with particular disease states will enhance the diagnosis and treatment of patients being screened for sleep-disordered breathing, or for monitoring patients already undergoing therapy. What is needed is an algorithm for flow data in the form of classifier.

What is particularly desirable is a method and apparatus for diagnosing Cheyne-Stokes breathing from flow readings or oximeter readings by use of appropriate software in conjunction with a small hand-held device for use in a home setting.

Diagnosis of Cheyne-Stokes Respiration ("CSR")

The diagnosis of CSR usually involves conducting a sleep study and analyzing the resulting polysomnography ("PSG") data. In a full diagnostic PSG study, a range of biological parameters are monitored that typically include a nasal flow signal, measures of respiratory effort, pulse oximetry, sleeping position, and may include: electroencephalography ("EEG"), electrocardiography ("ECG"), electromyography ("EMG") and electro-oculography ("EOG"). Breathing characteristics are also identified from visual features, thus allowing a clinician to assess respiratory function during sleep and evaluate any presence of CSR.

During a period of Cheyne-Stokes breathing or CSR, patterns of waxing and waning tidal volume can be seen in a nasal flow signal, which is a direct measure of pulmonary functions. This unstable behavior of breathing often extends its presence into other cardio-respiratory parameters such as blood oxygen saturation levels where cyclical changes can be seen.

While the examination by a clinician is the most comprehensive method, it is a costly process and depends heavily upon clinical experience and understanding. For effective and efficient screening of patients, a classifier algorithm has been developed by the assignee of this invention that automates the scoring process by calculating the probability of a CSR occurring based on a nasal flow signal. The algorithm is disclosed in US patent application Ser. No. 11/576,210 (U.S. Patent App. Pub. No. 20080177195) filed Mar. 28, 2007, and published as WO2006066337A1 Jun. 29, 2006. The existing algorithm is a flow-based classifier where a probability of CSR is calculated given a sequence of discrete flow values. A series of pre-processing steps are performed such as linearization of flow values, filtering and the extraction of respiratory events.

The concept of a classifier is common to many fields where it is desirable to assign an object or an underlying state of an object to one of a number of classes. This concept is used, for example, in the fields of voice recognition (where sound bytes are classified as different words or syllables), radar detection (where visual signals are classified as enemy/friendly targets) and medical diagnosis (where test results are used to classify a patient's disease state). The design of a classifier falls under the field of Pattern Recognition and a classifier can be of the supervised type (the classifier is built from training data which has been pre-classed by a supervisor or "expert") or unsupervised type (where the natural ordering or clustering of the data determines the different classes). Time signal classification usually relies on representing the signal at particular time points with "features". Features are simply numbers that distil the essence of the signal at a point in time, a form of compression. A set (or vector) of features is called a "pattern". A classifier takes a pattern and manipulates it mathematically with a suitable algorithm to produce a probability value for each of a number of classes. The pattern is assigned to the class with the highest probability.

Home pulse oximetry has been proposed as an alternative tool for identification of CSR, but relies on visual inspection of the oximetry signal by a trained observer (Staniforth et al., 1998, Heart, 79:394-99).

A study of 104 subjects with Congestive Heart Failure ("CHF") by Staniforth et al. (1998, Heart, 79, 394-399.) has examined the de-saturation index recorded in nocturnal oximetry compared to normal controls. The model yielded a specificity of 81% and a sensitivity of 87% for detecting CSR-CSA. However, the overall accuracy of the model was not provided. Those authors made no attempt to determine if pulse oximetry could be used to distinguish between CSR-CSA and Obstructive Sleep Apnea ('OSA'). U.S. Pat. No. 5,575,285—Takanashi et al, describes measuring oxygen saturation in blood from scattered and transmitted light and performing Fourier transformation to obtain a power spectrum over a frequency range of 500 Hz to 20 kHz. However, that described method does not allow for distinction between patients with CSR and OSA.

U.S. Pat. No. 6,839,581 to Grant et al, PCT Application No. WO 01/076459 and U.S. Published Patent Application No. 2002/0002327 are entitled "Method for Detecting Cheyne-Stokes Respiration in Patients with Congestive Heart Failure." They jointly propose a diagnostic method for CSR including performing overnight oximetry recordings and performing spectral analysis on the oximetry recordings. A classification tree or neural network based on parameters derived from a power spectral analysis determines the presence or absence of CSR.

U.S. Pat. No. 6,760,608 to Lynn is entitled "Oximetry System for Detecting Ventilation Instability." This patent describes a pulse oximetry system used to generate a time series of oxygen saturation values. The occurrence of certain patterns along the time series is used to indicate ventilation instability.

U.S. Pat. No. 7,081,095 to Lynn et al is entitled "Centralized Hospital Monitoring System for Automatically Detecting Upper Airway Instability and for Preventing and Aborting Adverse Drug Reaction". It proposes an automatic system of diagnosis of OSA in a computerized environment of a centralized hospital critical care system.

U.S. Pat. No. 7,309,314 to Grant et al is entitled "Method for Predicting Apnea-Hypopnea Index From Overnight Pulse Oximetry Readings." This patent proposes a tool for predicting an Apopnea Hypopnea Index ("AHI") for use in the diagnosis of OSA by recording pulse oximetry readings, and obtaining a delta index, oxygen saturation times and oximetry de-saturation events. A multivariate non-parametric analysis and bootstrap aggregation is performed.

U.S. Pat. No. 7,398,115 to Lynn is entitled "Pulse Oximetry Relational Alarm System for Early Recognition of Instability and Catastrophic Occurrences." The system described in this patent has an alarm triggered by the early recognition of likely catastrophic occurrences by detecting decreases in $O_2$ saturation coupled with either: a) decrease in pulse rate; or b) increase in respiration rate. The system of this patent is aimed at treating and detecting OSA.

None of these prior art systems are capable of reliably interpreting oximetric data to reliably discriminate OSAs from CSR and to develop a probabilistic value for such attempts at apnea discriminations.

SUMMARY OF THE TECHNOLOGY

The present technology enhances the discrimination of CSR based on oximetry. The technology may be applied to enhance the detection performance of a flow-based classifier technology system. Thus, it may enable the screening of CSR to become more accessible. For example, it may be implemented as an additional feature to the detection system described in U.S. patent application Ser. No. 11/576,210 filed Mar. 28, 2007, and published as WO 06066337A1 on Jun. 29, 2006. Optionally, the technology may also serve independently or as a stand-alone alternative when a flow signal or data therefrom is unavailable or of unfavorable quality.

The present technology may replace the current screening process with one that is generally more comfortable and easier to use for the patient, easier to administer for the physician and/or less costly to conduct the analysis.

While the present technology may be explained in terms of a sequential process or algorithm, it may be understood that the process or algorithm can be carried out using a non-linear, non-sequential, or non-staged process, or the order of the process may be changed. While this embodiment of the technology describes an entire process, aspects of the technology may relate to only a subset of that process.

A signal representative of respiration, such as an oximetry signal, may be recorded from a patient using a logging device which includes a data-acquisition system and a memory. The respiratory signal may be processed either on-board by the recording device or off-line using a computer.

The signal may be initially pre-processed. For example, the signal can be filtered to remove unwanted noise and, where appropriate, the baseline is zeroed. The signal may also be made linear depending on the transducer used to detect the respiration. In particular the technology may include a process for removing artifacts peculiar to oximetric measurements and for developing an oximetry signal quality indicator (QI) that may be used to determine a confidence level in the discrimination prediction.

In another stage the signal is divided into n epochs of equal length. The epoch length can be as long as the entire record or as short as is practicable to enable detection of respiratory patterns. In one example embodiment, the epoch length is 30 minutes.

A CSR-detection algorithm of the present technology alternatively or in conjunction with oximetry may use the nasal flow signal from a device such as MAP's microMesam® together with pattern recognition techniques to assign a probability of CS breathing to each 30 minute epoch of flow recorded.

The technology may provide a method for the calculation of an Event Feature. The method may also include the calculation of a Spectral Feature determined by, for example, Fourier analysis or by the use of Wavelet Transforms.

Another characteristic of CSR, namely saturation delay, may be used to provide a method for calculating the amount of delay of de-saturation and re-saturation delayed but in synchrony with breathing as a further indicator of CSR.

The technology also may involve a method for training a processor implemented classifier to discriminate CSR and for producing a probability value for each epoch segment of oximetric data for indicating the presence of CSR.

In some embodiments of the technology, a computer implemented method detects an occurrence of Cheyne-Stokes respiration with one or more programmed processors. The method of the processor may include accessing blood gas data representing a measured blood gas signal. It may also include determining a duration of one or more contiguous periods of changing saturation of a blood gas from the blood gas data. It may further include detecting the occurrence of Cheyne-Stokes respiration from a comparison of the determined duration and a threshold derived to differentiate saturation changes due to Cheyne-Stokes respiration and saturation changes due to obstructive sleep apnea. In some embodiments, the one or more contiguous periods of changing saturation may be re-saturation periods and the measured blood gas signal may be an oximetry signal. In still further embodiments, the determined duration may be a mean period length and the detecting may indicate an occurrence when the mean period length exceeds the threshold. In some embodiments, the threshold comprises a discriminant function. The detecting the occurrence may optionally involve determining a distance from the threshold and comparing the distance to a further threshold. The method may also optionally involve determining a presence of a peak in a predetermined frequency range for desaturation and resaturation cycles of the blood gas data and comparing the determined presence to the discriminant function.

Embodiments of the technology may also involve an apparatus to detect an occurrence of Cheyne-Stokes breathing. The apparatus may include a memory for blood gas data representing a measured blood gas signal. The apparatus may also include a processor coupled with the memory. The processor may be configured (a) to determine a duration of one or more contiguous periods of changing saturation of a blood gas from the blood gas data and (b) to detect an occurrence of Cheyne-Stokes respiration from a comparison of the determined duration and a threshold derived to differentiate saturation changes due to Cheyne-Stokes respiration and saturation changes due to obstructive sleep apnea. In some embodiments of this apparatus, the one or more contiguous periods of changing saturation may be re-saturation periods when the measured blood gas signal is an oximetry signal, which may be measured by an optional oximeter. In some embodiments, this determined duration may be a mean period length and the detecting may indicate an occurrence when the mean period length exceeds the threshold, which may optionally be a discriminant function. In processor apparatus may also be configured to detect the occurrence by further determining a distance from the discriminant function and comparing the distance to a further threshold. In still further embodiments, the processor can be configured to determine a presence of a peak in a predetermined frequency range for de-saturation and re-saturation cycles of the blood gas data and then compare the determined presence to the discriminant function.

The CS diagnosis system of the present invention may use pattern classification techniques on a digital computer to identify periods of CS-like breathing by examining the flow signal alone. Ordinarily the definitive diagnosis of CS breathing relies on an "effort" signal, either esophageal pressure or an elastic band signal from the abdomen or thorax. An absence of effort denotes a central apnea which may otherwise be difficult to distinguish from an obstructive apnoea or a mixed apnoea. A mixed apnoea is comprised of a central beginning (without effort) followed by a section of obstructed breaths once drive returns.

ApneaLink™ nasal flow data without other channels is processed to classify it as unambiguously Cheyne-Stokes (CS) breathing or nearly so and to then display a likely record to the physician for quick expert confirmation. An ApneaLink™ recorder is a single channel battery-powered respiratory pressure sensor system and provides recordings of respiratory pressure during sleep. The ApneaLink™ is a small (hand held) device manufactured by ResMed, designed for use in a home setting where it is worn strapped to the patient's chest. The device only records nasal flow (indirectly) using a nasal pressure-sensing catheter. All relevant respiratory information during sleep will be collected via nasal pressure cannula. This will allow cardiologists to manage such patients more expediently. For example, CS patients would go on to a full polysomnogram (PSG) workup for possible AutoSet CS therapy as appropriate. Non-CS patients might just go on to AutoSet to treat the underlying OSA as appropriate. After suitable offline processing of the nasal flow signal using a PC, the following events can be detected and displayed: apnoeas, hypopnoeas, flow-limitation and snore.

The CS-detection algorithm uses the nasal flow signal from a device such as ResMed's ApneaLink® or other signal indicative of at least one respiratory parameter together with pattern recognition techniques to assign a probability of CS breathing to each 30 minute epoch of flow recorded. This invention details the initial filtering and "event" detection, where events are defined as regions of hypopnoea-hyperpnoea sequence characteristic of CS breathing. The detection of such events may be determined from the duration of one or more regions of hyperpnoea when the duration of the hyperpnoea exceeds a threshold. or a statistic of the duration of regions of hyperpnoea exceeds a threshold. Such a statistic may be an average or a standard deviation or other statistics specified below.

Pattern classification techniques are statistical and rely on a so-called "training" data set by which a "classifier" can be trained to recognize certain "patterns", in this case CS breathing. A pattern is a group or vector of features. A feature is a number which represents some aspect of the signal being examined. An example of a feature is apnoea length. A pattern might be the group comprising apnoea length, hyperpnoea length and a number representing the closeness of the shape of the hyperpnoea to a "harbor bridge".

One aspect of the invention is directed to a method and apparatus or system capable of better diagnosing the presence of sleep disorders, preferably with a higher level of confidence. The diagnosis may comprise analyzing a signal indicative of a respiratory parameter to determine a rate of increase of the signal in the region from hypopnea to hyperpnoea and where the rate of increase is a slow increase, concluding that Cheyne-Stokes breathing is present and where the rate of increase is a sudden increase, concluding that Cheyne-Stokes breathing is absent.

According to one aspect of the invention, a signal representative of a patient's respiration is split into equal length epochs which can be as long (the entire record) or as short (the length of a representative hypopnoea-hyperpnoea sequence) as desired. Preferably, the signal will be subject to a number of pre-processing steps in order to filter out noise and zero the baseline, for example.

Preferably, from each epoch one or more primary features is extracted from the signal that act as a compressed representation of the signal events. By events it is meant: e.g., apneas, hypopnoeas and hyperpnoeas. Statistics are applied to the primary feature(s) to produce one or more secondary features which represent the entire epoch. Each secondary feature is grouped with one or more other features that is extracted from the entire epoch rather than from the epoch events. This final group of features is the epoch pattern.

The epoch pattern is preferably manipulated with a suitable classifier algorithm to produce a probability for each possible class that the signal may be representative of (e.g. Cheyne-Stokes breathing, OSA etc.). The epoch is assigned to the class with the highest probability and the class and the strength of the probability can be reported as an indication of the underlying disease state.

The classifier algorithm is preferably learned from a training data set which has been pre-classified by a human expert. In this sense the classifier is of the supervised machine learning type.

Other features of the technology will be apparent from consideration of the information contained in the following detailed description, abstract and claims.

BRIEF DESCRIPTION OF THE DRAWINGS

The present technology is illustrated by way of example, and not by way of limitation, in the figures of the accompanying drawings, in which like reference numerals refer to similar elements including.

DETAILED DESCRIPTION

Figure 1:
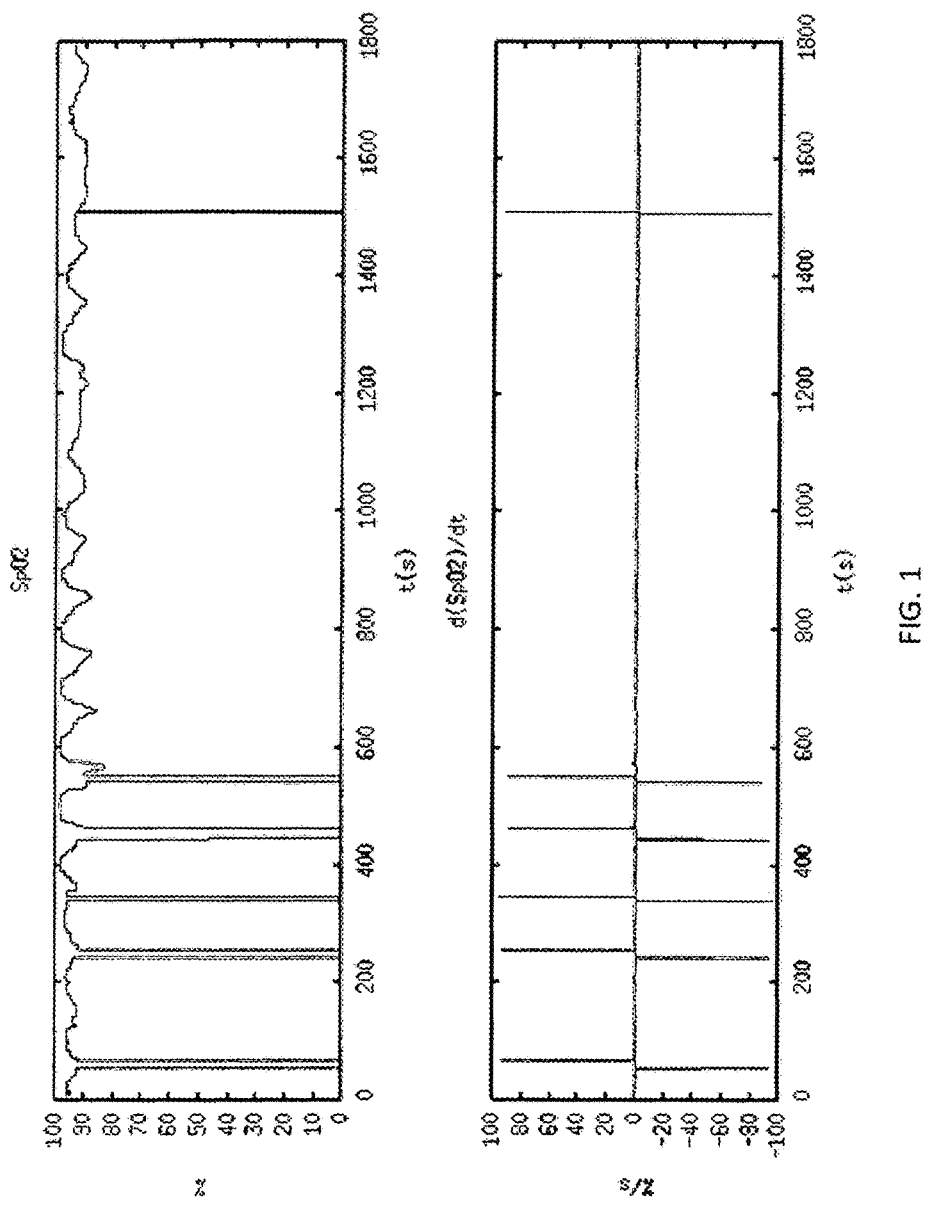
FIG. 1 is an example graph of the amplitude and first difference of an oximetry signal in a patient over a duration of one half hour (1800 seconds)

Embodiments of the present technology may include: a system, device, classifier, and/or methods. Example embodiments are herein described with reference to the accompanying drawings and more specifically FIGS. 1-13 and 15.

CSR is a form of periodic breathing believed to be due to instability in the central nervous system control of ventilation. Breathing in a CSR sufferer is characterized by a "waxing and waning" tidal volume as respiration alternates between repetitive episodes of apnea/hypopnea and hyperpnea. Recordings of nasal flow signals in a compressed time scale reveal a pattern that is similar to an Amplitude-Modulated ('AM') waveform.

During a period of Cheyne-Stokes breathing or CSR, the pattern of waxing and waning tidal volume that can be seen in a nasal flow signal as a direct measure of pulmonary function also is present as cyclical changes in other cardio-respiratory parameters such as blood oxygen saturation levels. For example, during sustained apneic periods, blood oxygen saturation may fall due to the dynamics of the cardio-respiratory system. Measurements of oxygen saturation using pulse oximetry exhibit periodic de-saturation and re-saturation that mimics the rise and fall of ventilation caused by CSR.

The cyclical pattern of the blood oxygen saturation levels in CSR differs to that of a serially occurring sequence of Obstructive Sleep Apnea (OSA) events. The patho-physiologic mechanism behind the Cheyne-Stokes breathing pattern is associated with the level of arterial partial pressures of carbon dioxide ($PaCO_2$). The presence of a low $PaCO_2$ may suppress patient's central drive to breathing in response to hypocapnia, which typically initiates shallow breathing and subsequently partial or complete withdrawal of breathing if driven below the apneic threshold, resulting in Central Sleep Apnea (CSA). Following an apneic period, a subsequent rise in $PaCO_2$ will develop, which may induce a hyper-ventilatory response. Consequently, a decline in $PaCO_2$ may begin where the cycle would normally repeat.

This oscillating response to ventilation may result in a waxing and waning tidal volume and a gradually swinging blood oxygen saturation levels. The rising and falling oxygen saturation levels are delayed but may usually be in synchrony with hyperventilation or hypoventilation. The underlying oscillation in the central respiratory drive in association with the cardiac and pulmonary interactions give rise to an oscillation in oximetric recording that are uniquely regular during CSR. The spectral feature is intended to capture this pattern of regularity in the oximetry signal as a marker of the CSR.

Evidence suggests that a compromised cardiac function is a risk factor to contributing to CSA. In the stable Congestive Heart Failure (CHF) population, prevalence rates of CSA ranging from 30% to 50% has been reported (Javaheri et al., Circulation. 1998; 97:2154-2159; Sin et al., Am J Respir Crit Care Med 1999; 160:1101-1106.). It has also been supported that a high apneic threshold of $PaCO_2$ predisposes a development of CSA and CSR.

A period of pure Cheyne-Stokes breathing is commonly presented in a PSG study as a serially occurring sequence of CSA events. The development of CSA constituting pure Cheyne-Stokes breathing is non-hypercapnic in origin with typical cycle lengths of 60 seconds (Eckert et al., Chest, 2007; 131:595-607). It is to be differentiated from other forms such as idiopathic CSA or narcotic-induced CSA arising from the application of chronic pain medications. These forms of CSA typically have a much shorter cycle length. The selection of oximetric recordings used for the training of the classifier excludes such data as would be assessed and screened by the clinical expert during the pre-scoring process. This ensures only specific forms of CSA of interest are used for the training of the classifier.

CSR Versus OSA:

Cheyne-Stokes Respiration (CSR) is a form of periodic breathing that is typically observed through direct measurement of pulmonary functions such as a nasal flow recording or airway flow recording. Due to the coupling between the cardiac and pulmonary system, CSR may also be identified as alternating periods of desaturation and resaturation through an oximetry signal. Thus oximetry signals may provide a source of information available for the analysis of Cheyne-Stokes breathing. Benefits of this approach may include the use of oximeters for non-invasively measuring blood oxygen saturation levels, which is an important determinant of a subject's health condition. While oximetry recordings may provide evidence of the occurrence of CSR, or other breathing abnormalities which may also be reflected in an oximetry signal such as conditions of Obstructive Sleep Apnea (OSA). This is preferably taken into account during the training of the classifier to discriminate CSR from OSA.

OSA may be generally initiated by the collapse of the upper airway. During an OSA event, the central drive to breathing is not withdrawn as can be seen from the continuing respiratory effort during a PSG study. Initial breaths following an OSA event is typically deep in effort with large tidal volume, which is often associated with a rapid rise in oxygen saturation level. In a serially occurring sequence of OSA events, rapidly re-saturating oxygen saturation levels is thus believed to be indicative of an occurrence of OSA.

The occurrence of an OSA event is closely related to the mechanical state and anatomy of the upper airway. OSA is driven by the collapse of the pharynx, which may happen in a recurring manner but unlike CSR, it is not a form of periodic breathing. The variability in the length of time from the onset of a preceding OSA event to the onset of its successive OSA event tends to be shorter than the cycle lengths of CSR. Oximetry from an OSA recording may find a more episodic pattern of desaturation and re-saturation, lacking the typical regularity found in the cycle lengths of a pure CSR oximetry recording.

However, oximetry signals are contraindicated for use in diagnosing CSR by being prone to undesirable artifacts caused by body motion or limb movements. In adult recordings, oximeters are commonly placed at the fingertip or ear lobe. The quality of the oximetry signal is highly sensitive to any displacement of the optical sensor in an oximeter. Motion artifacts are typically characterized by periods in which abrupt de-saturation and sharp re-saturation occur. It is not uncommon to find that saturation levels are at zero percent within an artifactual period of oximetry recording. There may be a loss of information during this period, which may be unavoidable. This issue may be overcome by modifying the use of an oximetry signal to incorporate a detection scheme that takes into account the abruptness of de-saturation and re-saturation.

FIG. 1 depicts an example of an oximetry signal 102 and the derivative thereof or a derived oximetry signal 104 from a recording. The signal was recorded during CSR over the duration of a half hour (1800 seconds). Clear instances of artifacts are shown as the plunge to zero saturation and the sudden recovery. In a system or device of the present technology, data from the signals may be processed according to one or more of the following methodologies.

Identifying Artifacts

From the derived oximetry ($SpO_2$) signal 104 the beginning of an artifactual period where the signal goes from a negative value of less than −10% to a positive value of greater than 10% may be identified. The derived oximetry signal provides an indication of the beginning and end of an artifactual period, which is marked by an initial sharp negative spike followed by an abrupt positive spike. Artifacts may be removed by linearly interpolating across the region of artifacts.

Oximetry Signal Quality Indicator (QI)

Whereas oximetry measurements have been employed for the detection of OSA, those detection methods are not transferable to the problem of detecting CSR. The presence of CSR indicates central instability in ventilatory control. In pure Cheyne-Stokes breathing flow is often associated with central apneas and hypopneas. In contrast to obstructive apneas, the resumption of breathing in CSR is usually very gentle, which leads to a slower rate of re-saturation. The present technology takes into account this difference between OSA and CSR, by making use of the mean re-saturation period and the fact that our statistical analysis shows that only CSR demonstrates re-saturation longer than 10 seconds.

A quality indicator may be defined for a derived oximetry ($SpO_2$) signal 104 by finding the number T of samples thereof where SpO2 drops below a predetermined percentage threshold such as 10%. The quality indicator (QI) may be defined as the ratio of T/N where N is the total number of samples considered. However, if this ratio is less than a threshold of, for example, about 0.75, the quality indicator may be set to zero. It is also possible to define the quality indicator as a function of the ratio T/N.

Calculation of an Event Feature

Once the artifacts have been identified they may be removed from the data. A signal of the remaining data may also be low-pass filtered to derive a filtered signal. The signal can be filtered first to remove unwanted and uninteresting high-frequency content. For example, the filter used may be a digital Finite Impulse Response ("FIR") filter designed using the Fourier method with a rectangular window. In some embodiments, the filter may have a pass-band from 0 to 0.1 Hz, a transition band from 0.1 to 0.125 Hz and a stop band above 0.125 Hz. The number of terms in the filter varies with sampling frequency. The signal may be filtered by convolving the time series point-wise with a filter vector.

Next contiguous periods of re-saturation may be detected. The length of the period may be stored as components of a vector. The event feature may then be calculated as the mean of the components of the vector. The event feature can be associated with a quality indicator value. Thus, it may be output with a CSR determination based on the particular event feature to provide information to a clinician as to the quality of the CSR detection.

One alternative to extract an event from an oximetry signal may be to derive two filtered signals and then perform a comparison of their varying amplitudes to frame a desaturation event or resaturation event. The filter for the first of these derived signals shall have a very low cut-off frequency to represent the long-term saturation signal (SLong). The filter for the second of the derived signals may have a relatively higher cut-off frequency to represent the short-term saturation signal (SShort). When SShort falls below a threshold as a percentage of SLong, this may be taken as a trigger for recording the start of the desaturation event. When SShort subsequently rises above a threshold above SLong, this may be taken as a trigger to record as the end of the desaturation event. A similar process maybe applied to capture a resaturation event.

Calculation of a Spectral Feature (SF)

Figure 2:
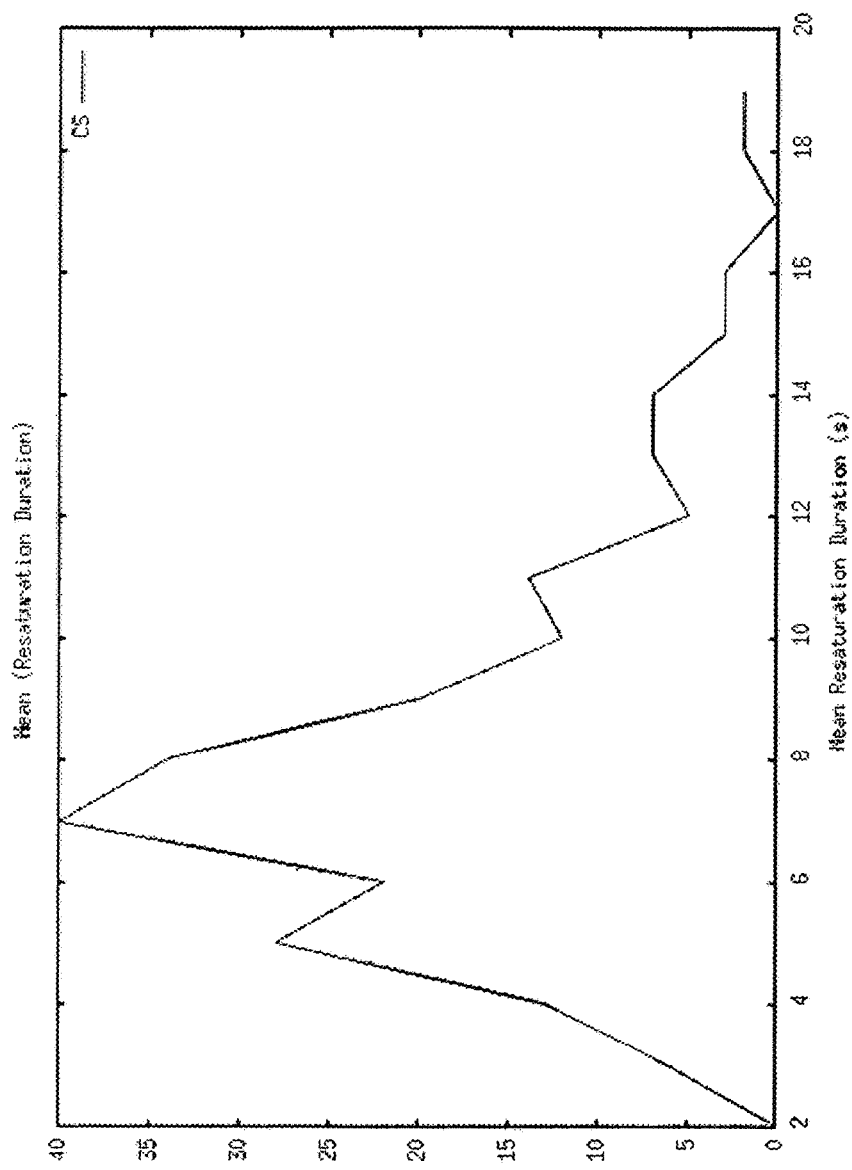
FIG. 2 shows the mean saturation duration in CSR as a function of time measured in seconds.
Figure 3:
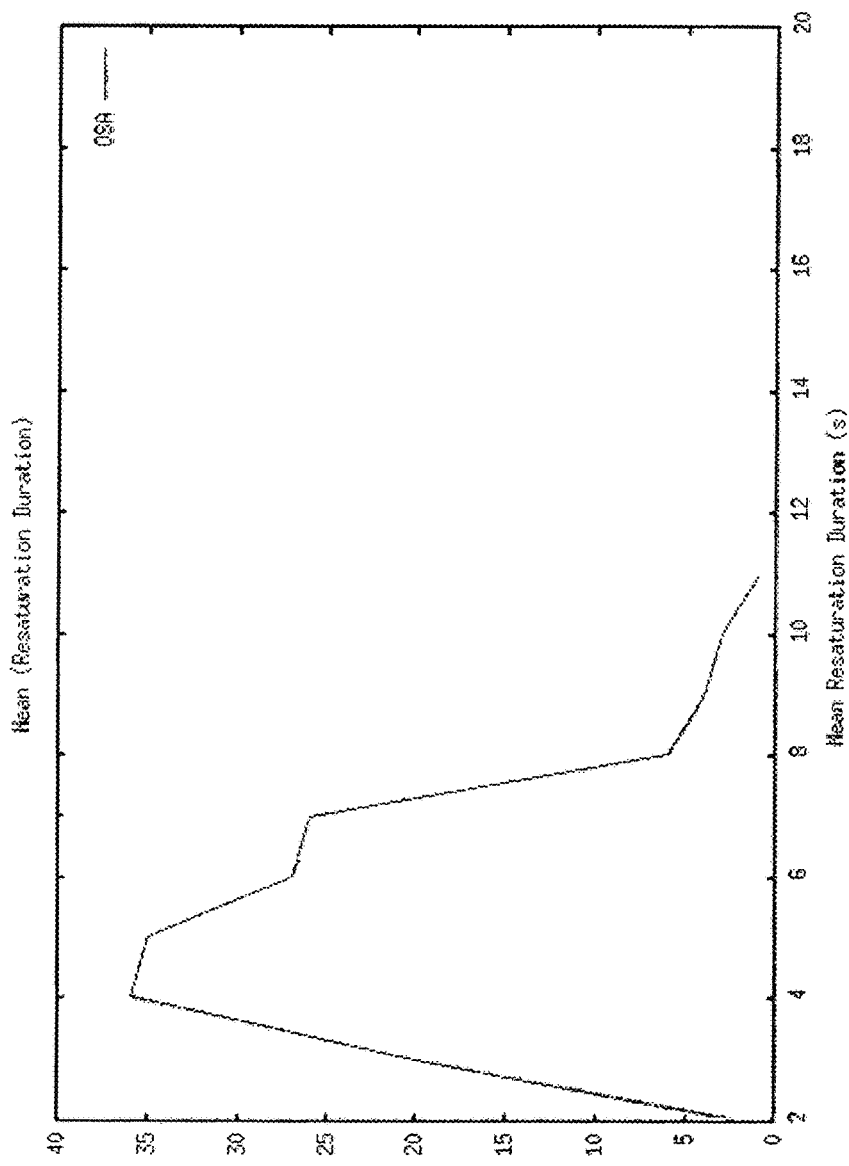
FIG. 3 shows the mean saturation duration in OSA as a function of time measured in seconds.
Figure 4:
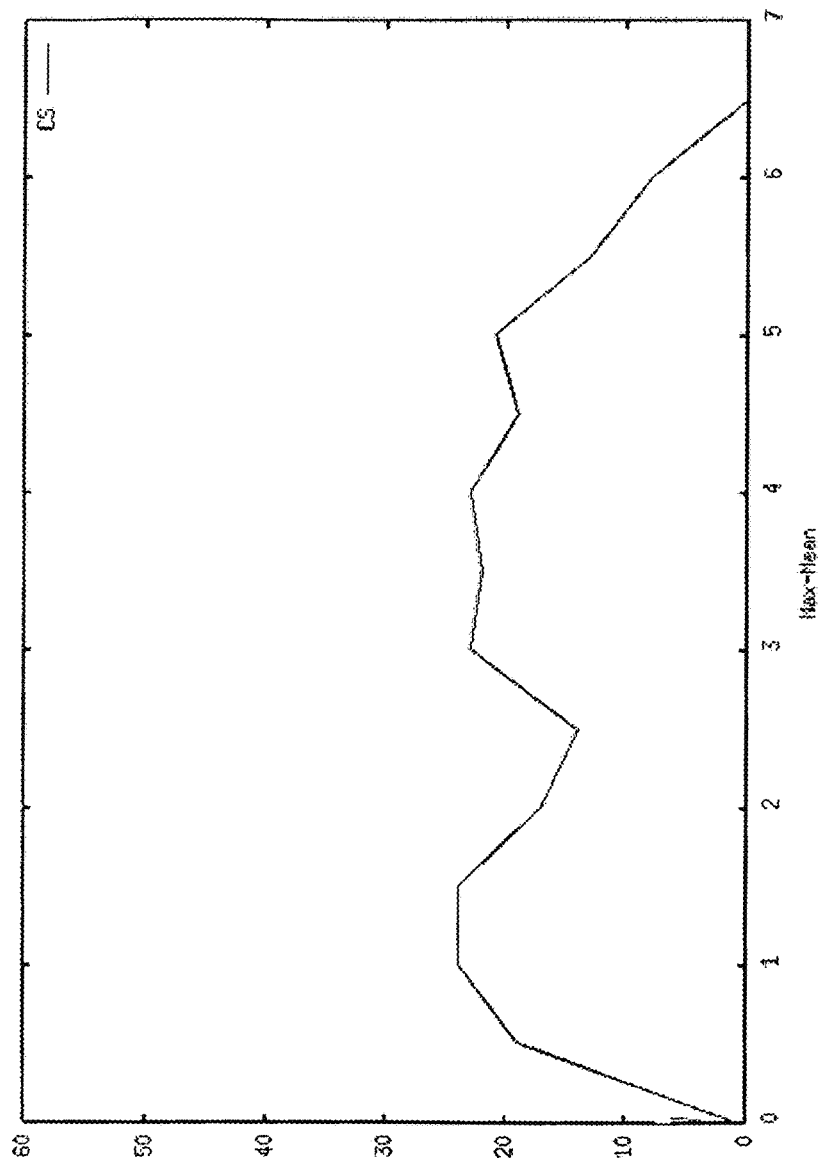
FIG. 4 shows the spectral feature of CSR, where the spectral feature is the difference between the maximum and mean value of the Fourier Transform of the saturation.
Figure 5:
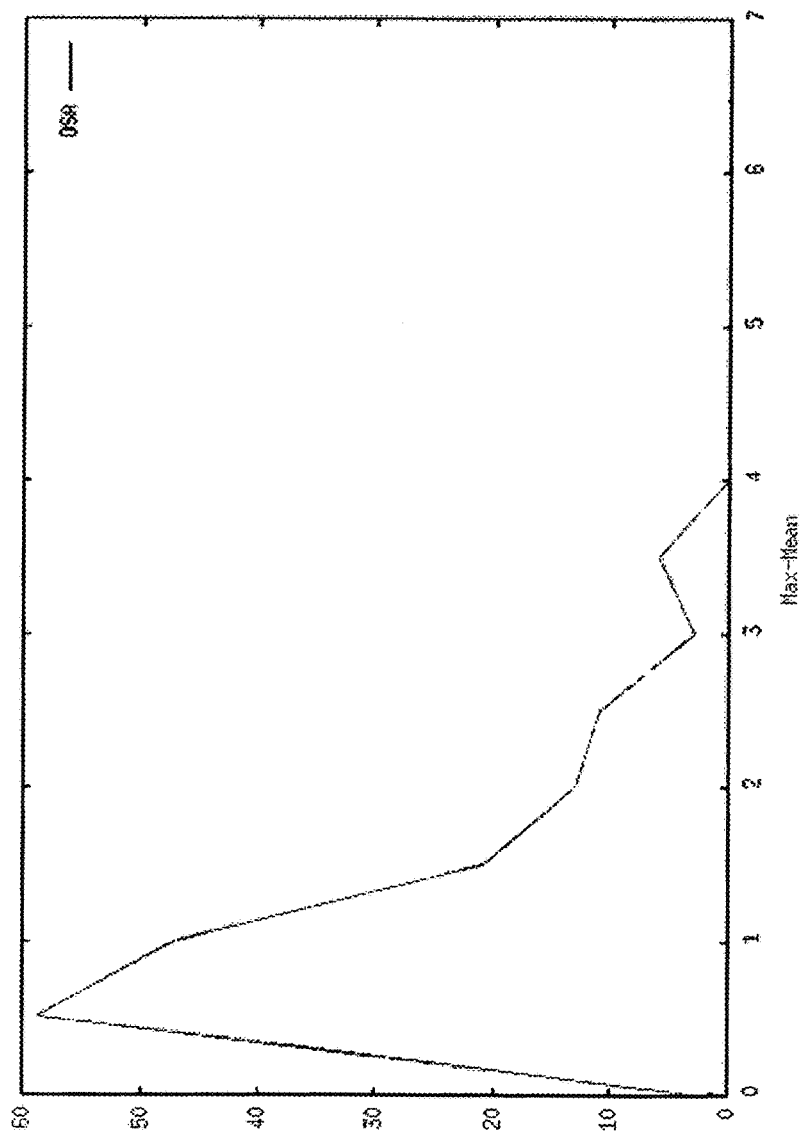
FIG. 5 shows the spectral feature of OSA, where the spectral feature is the difference between the maximum and mean value of the Fourier Transform of the saturation.

The periodic alternation between apnea/hypopnea and hyperpnea often leads to desaturation and resaturation that are delayed but in synchrony with breathing. The observed oscillation in SpO2 depends on multiple factors, one of which is the duration of an apnea. Longer apneas are associated with greater desaturation. FIGS. 2 & 3 show the distribution of mean saturation duration in CSR (FIG. 2) compared to those of OSA (FIG. 3) as a function of time measured in seconds. Observation of various CSR oximetry patterns finds a higher regularity, in contrast to the episodic nature of oximetry patterns during continuous periods of obstructive apneas. Using a Fourier transform, a spectral feature may measure the presence of a peak in the region near 0.083 Hz to 0.03 Hz.

The tendency to de-saturate and re-saturate over longer cycle times may be taken as a marker of a CSR abnormality. This may be detected or recognized using Fourier-transform techniques to determine individual frequency components and harmonics. Rapid resaturation during post-apneic termination of an OSA event with deep arousal breaths gives a more episodic style of desaturation and resaturation patterns. This distinguishes the frequency characteristics from the more regularly de-saturation and re-saturation patterns of CSR.

In some embodiments, some or all the following example steps may be implemented to determine a Spectral Feature using a Fourier-Transform analysis:
1. Remove artifacts
2. Divide the entire oximetry signal into discrete 30 minutes, 50% overlapping epochs
3. Subtract the signal from 100%
4. Subtract the resulting signal from an initial value and store this value
5. Low-pass filter the resulting signal
6. Add the initial value stored back to the filtered signal
7. Subtract the resulting signal from 100%
8. De-trend the signal by the mean value
9. Normalize the resulting signal using the Euclidean norm
10. Calculate the spectrogram with five half-overlapping epochs
11. Take the real and absolute magnitude of the spectrogram
12. Extract the 0.083-0.03 Hz region and form a new vector
13. The Spectral Feature (SF) is calculated as the difference between the maximum and the mean value FIGS. 4 & 5 respectively depict the distribution of the spectral feature for CSR and OSA as the difference between the maximum and mean value of the Fourier-Transform as just described.

Use of Wavelet Transforms

Figure 6:
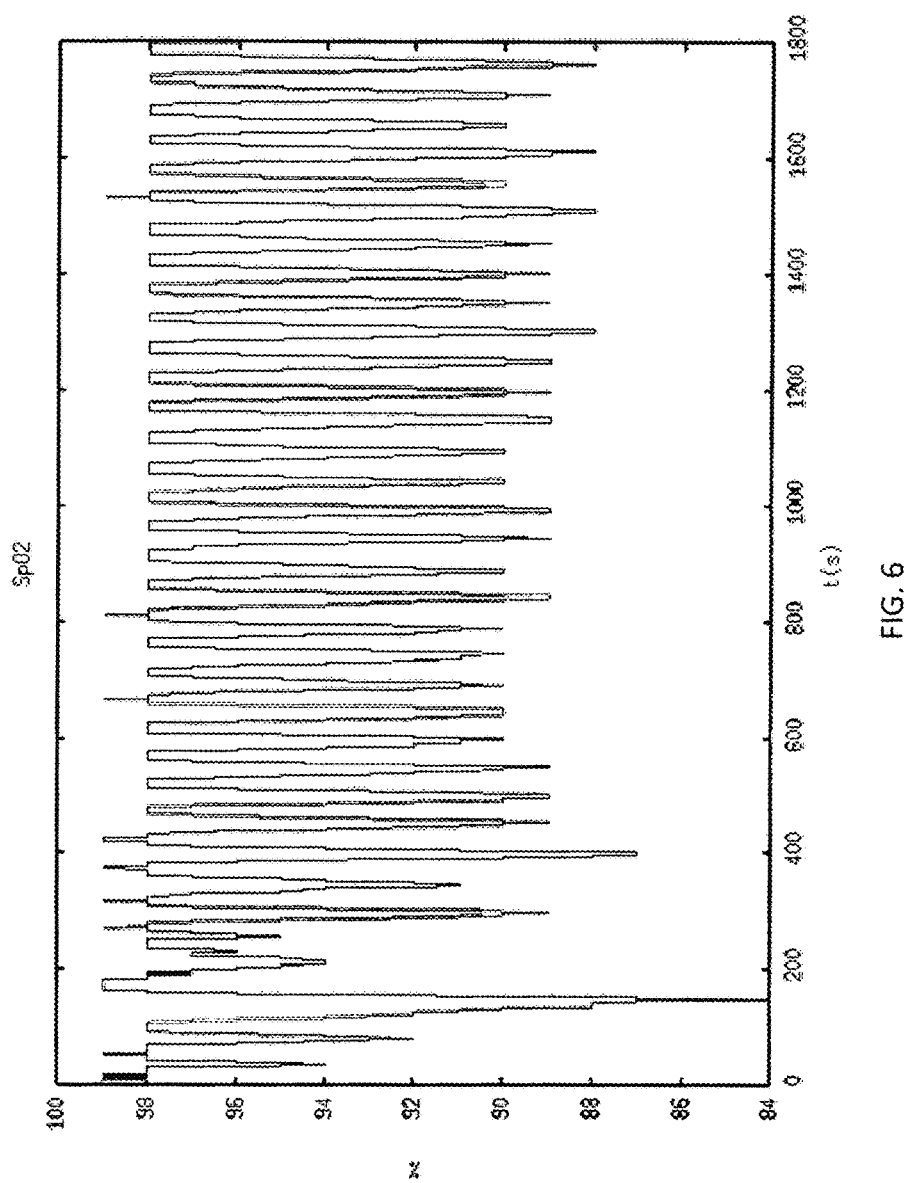
FIG. 6 shows the oxygen saturation of representative CSR epochs.
Figure 7:
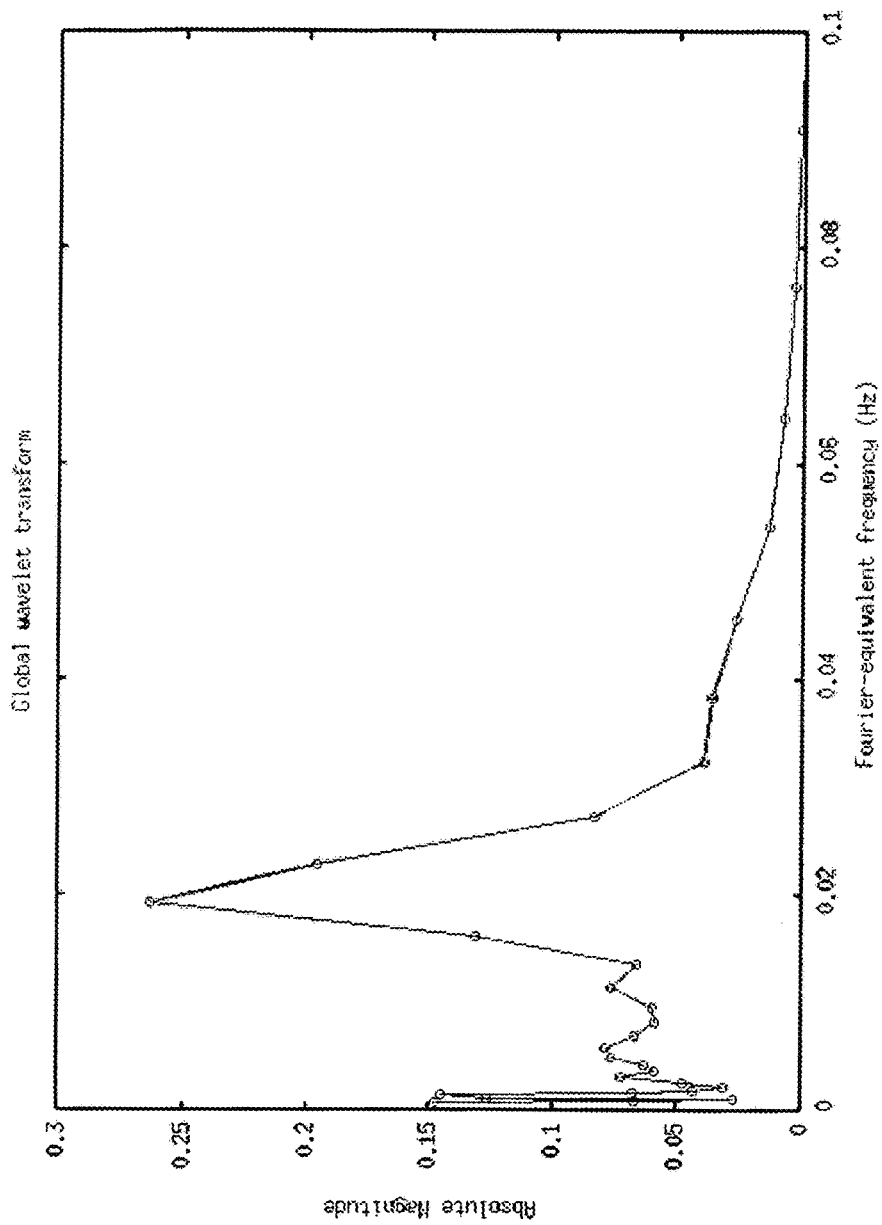
FIG. 7 shows the global wavelet spectrum of CSR as a function of the Fourier-equivalent frequency.

Continuous wavelet transform may also be applied to give time-frequency information over the duration of the signal. FIG. 6 shows the oxygen saturation with CSR occurring in a representative epoch E1 In such CSR epochs, the wavelet-transformed data often results in a ridge that can be found or detected in the 2-dimensional data. The wavelet spectrum can be translated from the scale domain (dimensionless) into Fourier-equivalent frequency (Hz) depending on the type of wavelet transform used. FIG. 7 shows the global wavelet spectrum as a function of the Fourier-equivalent frequency using the Morlet wavelet as the wavelet function. Epochs with strong presence of CSR often find a spectral peak around the 0.02 Hz Fourier-equivalent region. This corresponds well with the Fourier-based spectral peak, as seen in FIG. 7. Thus, in some embodiments of the technology, the peak of the global wavelet spectrum may also be used as a spectral feature for the analysis of CSR in oximetry signal.

Delay of Saturation

The periodic alternation between apnea/hypopnea and hyperpnea often leads to desaturation and resaturation that are delayed but in synchrony with breathing. This Delay of the Saturation ("DoS") level response is a result of the complex cardio-respiratory dynamics. Some or all of the steps of the following method may be used in some embodiments to extract the delay algorithmically.
1. Square the flow signal
2. Low-pass filter the squared flow signal
3. Square-root the resulting signal
4. Down-sample the signal to the equivalent frequency of the oximetry signal to give the ventilation signal
5. Normalize the ventilation signal by the absolute maximum value
6. Subtract the oximetry signal from 100%
7. Normalized by the absolute maximum value
8. Subtract the SpO2 signal from 1.0
9. Cross-correlate the normalized SpO2 signal with the down-sampled and normalized ventilation signal
10. Find the offset to the maximum cross-correlation attained
11. Calculate the delay in samples as the number of samples from the last index of the SpO2 signal
12. Divide the delay in samples by the sampling rate to get the delay in seconds Optionally, as an alternative to the aforementioned squaring and square root operations being performed on the flow signal in steps 1 and 3 above, an absolute value operation on the flow signal may be implemented.

Figure 8:
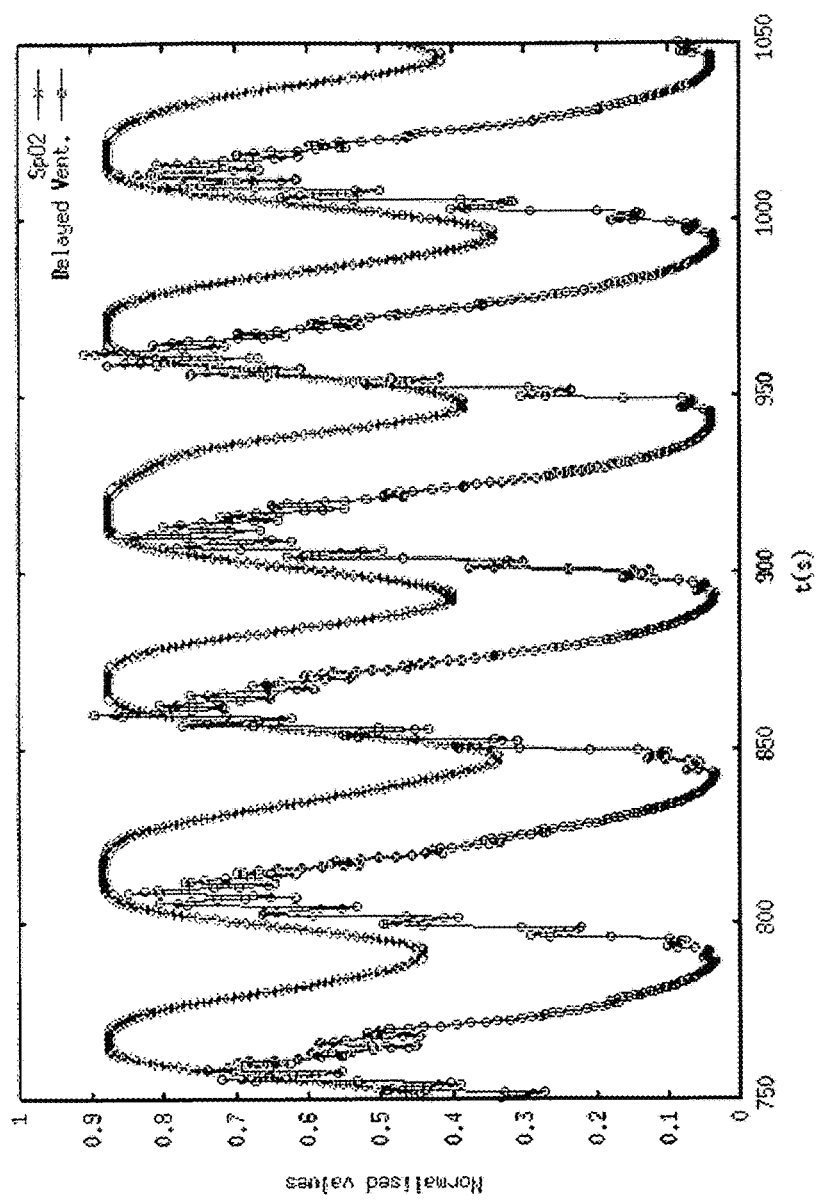
FIG. 8 shows the computed delay for oxygen saturation, ventilation and delayed ventilation as a function of time in seconds.

FIG. 8 shows a result of such a calculation by plotting a filtered SpO2 signal as a function of time in seconds and the shifted ventilation signal using the computed delay.

Training a Classifier to Discriminate CSR

The event feature and the Fourier-based spectral feature may be selected to train a classifier of the present technology. Training for an example embodiment was performed using 90 Embletta recordings of clinical diagnostic studies.

Two independent sets of polysomnographic (PSG) data were used for the development of the algorithm of a classifier. The first set (which is herein referred to as the EssenEmbla study) was a diagnostic clinical trial conducted at a sleep facility in Essen, North-Rhine Westphalia; Germany, involving 90 patients presenting with Central Sleep Apnea (CSA), OSA, and a combination of both. The EssenEmbla study was used as the training set. The second set (BadO) was conducted in Bad Oeynhausen, North-Rhine Westphalia, Germany. The prevalence of the BadO data set also contains recordings of CSA, OSA and a combination of both. These are 8 hours of overnight recordings that were then used as the test set to evaluate the classifier after a training session.

To facilitate the training of the algorithm of the classifier, initially both sets of data had been pre-classified by a clinician. Each of the recordings were scored by the resident clinical expert at ResMed in 30 minute segments, where a designation of predominant event is made by means of offline visual inspection through a computer with PSG software. The events were designated into one of five general types of events:
 1. No apnea
 2. CSR
 3. OSA
 4. Mixed apnea
 5. Combination of events As a result of this pre-classification process, each 8-hour recording yielded 16 non-overlapping epochs in total, each with a specified class of dominating event. In the EssenEmbla training set where 90 patients were involved, there was a total of 1440 classes of data available for training. Any residual epoch less than 30 minutes was not assessed. Nevertheless, the residual epoch may optionally be any period greater than several breath cycles of the patient. For example, the residual epoch may be greater than 5 minutes. The most preferred residual epoch may be 30 minutes.

During this pre-scoring process, the clinical expert utilized any of the available PSG channel recordings to assist in determining the predominant events and assigning a designation to each of the half-hour segment. These included the nasal flow, digital oximetry, measures of respiratory effort, sleeping position by means of gravitational indictors, heart rate, electroencephalography (EEG), electrocardiography (ECG), electromyography (EMG) and electro-oculography (EOG). Using the pre-classified designation of the training set, the oximetry and flow recording was segmented with a computer processor and software into strict 30 minute non-overlapping epochs of data for analysis. Selected epochs of specific pre-classified events were then used for exploring specific features to be used as indicators of CSR. By pre-classifying the data into half-hour epochs, the quantitative significance of particular short-term features was not diluted over the length of the entire recording.

The division of time for each epoch was based upon giving consideration to the typical occurrence and lengths of each CSR event. For a higher than average 90 seconds cycle length of waxing and waning pattern of CSR, assuming the oxygen saturation de-saturates and re-saturates at a similar pace, there are 20 continuous cycles of CSR that can be captured within half an hour, which was sufficient for analysis. According to the American Academy of Sleep Medicine (AASM) 1999 published guidelines for standards of PSG diagnostic criteria, mild obstructive sleep apnea (OSA) defined as where on average between 5 to 15 events per hour of greater than 10 seconds cessation of breathing is found in a recording. In a 30 minute epoch with the presence of mild OSA, there will be at minimum 2.5 events within half an hour.

The decision boundary was formed using a Bayesian classification technique. This method is appropriate for normally distributed data and aims to find a discriminate that optimally separates the two classes (CSR and non-CSR) with minimum risks. Other classification methods may also be used to derive the decision boundary. Such examples may include neural networks or the k-nearest neighbor scheme.

Figure 9:
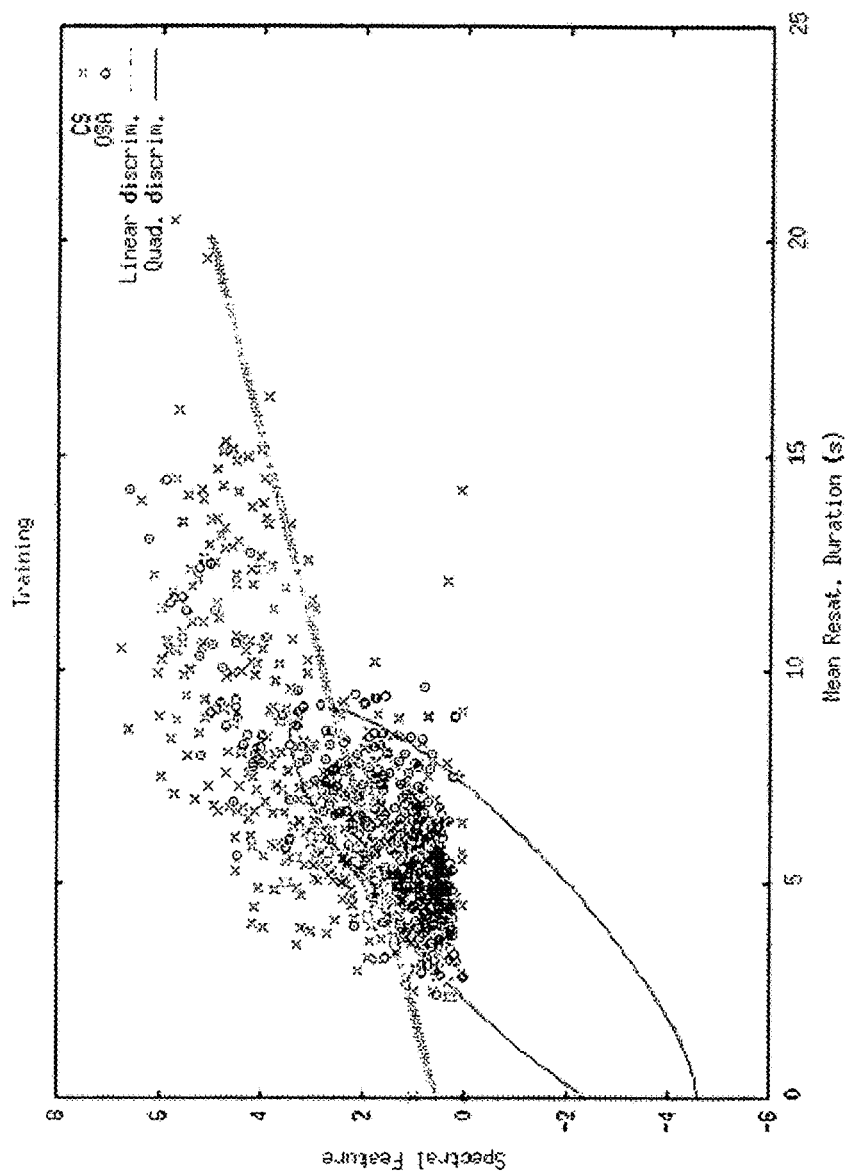
FIG. 9 depicts a decision boundary and its relationship to the distribution of the training set of data.

FIG. 9 illustrates the decision boundary and its relationship to the distribution of the data after training on an epoch-by-epoch basis. The straight line represents the linear discriminant function and the elliptical line represents the quadratic discriminant function following Bayesian classification. The discriminant function divides the space into regions of CSR and non-CSR.

Figure 10:
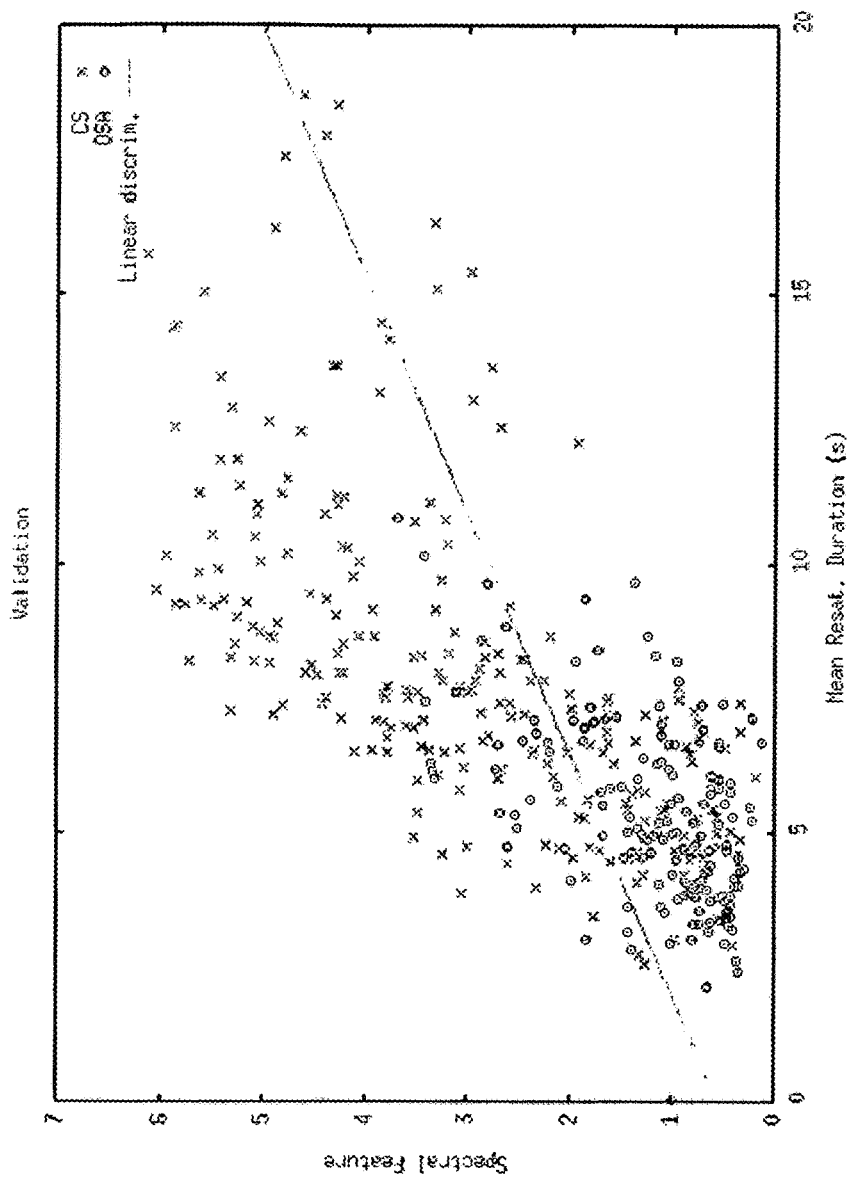
FIGS. 10 and 11 depicts the decision boundary and its relationship to the distribution of the validation set of data.
Figure 11:
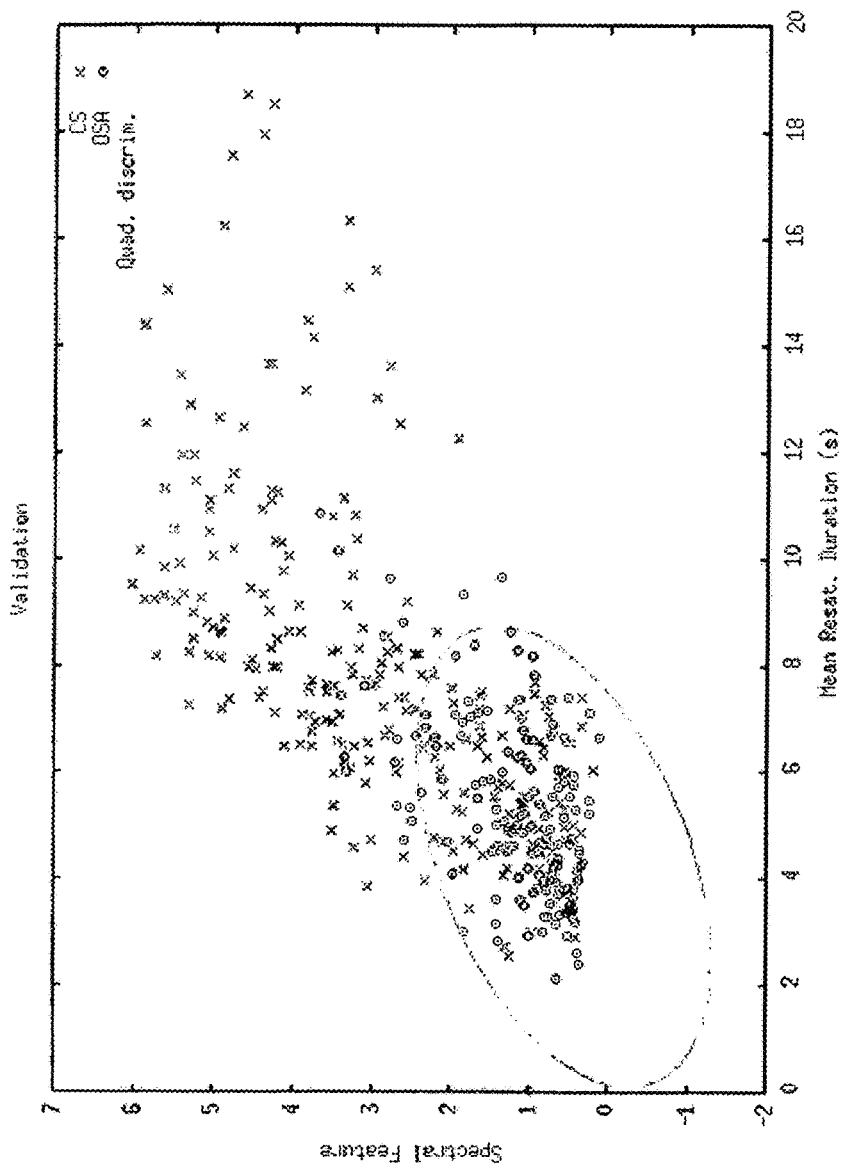

FIGS. 10 and 11 illustrate the trained decision boundary applied to the validation test data set on an epoch-by-epoch basis. The overall probability for the entire SpO2 recording may be derived using the following series of steps.
 1. Calculate the probability by mapping the perpendicular distance to the decision boundary using the sigmoid function $$p = \frac{a^d}{1+a^d}$$

2. If the probability is greater than a specified threshold such as 0.5, then the epoch will be classified as the CSR.
 3. If any of the epochs are classified as CSR, the oximetric recording will be classified as CSR-probable.

Figure 12:
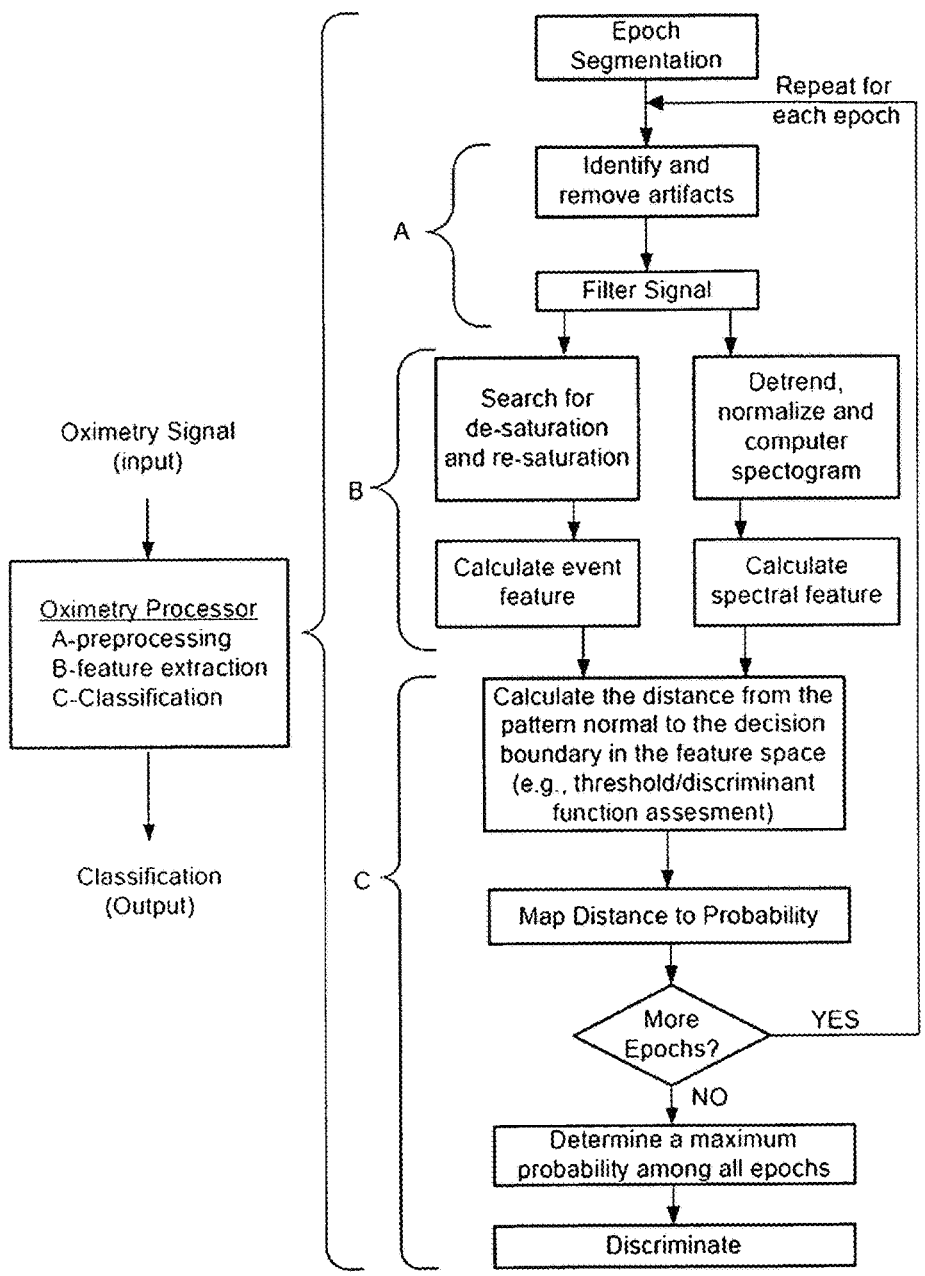
FIG. 12 is an example flow chart for process steps involved in modifying the distribution of data or classifying oximetry epochs for CSR.

FIG. 12 is a flow chart of example steps just described for feature extraction and classification. Such a methodology may be implemented as software or in the circuits or memory of a detection device as further illustrated in FIG. 15.

Patient-by-Patient Classification and Results

Probability Values

To get an understanding of how well the classifier discriminates CSR on a patient-by-patient basis, although it may be implemented to do so, instead of simply determining a binary output (CSR or non-CSR) for each epoch, the classifier may be implemented to produce a probability value of between zero and one for each epoch segment. For each derived mean resaturation duration and spectral feature, calculate the distance normal from the data point in the feature space to the decision boundary. This perpendicular distance is then mapped to a probability value where the probability is a function of the distance from the decision line.

$$p = \frac{e^d}{1+e^d}$$

If the distance is zero i.e. (d=0) the feature value would coincide with the boundary, then the probability is exactly 0.5. As the distance increases to positive infinity, the probability asymptotically tends towards 1.0. As the distance increases to negative infinity, the probability asymptotically tend towards 0.0. By defining the region of feature space corresponding to CSR as positive distance from the discriminant in this embodiment, CSR may be defined as any resulting probability value of greater than 0.5. It will be recognized that the technology may be implemented to yield other values for distinguishing the presence of CSR with distance from such a discriminant function.

In the process of classifying an oximetry recording on a patient-by-patient basis, a processor implemented algorithm embodying the classifier may be programmed to iterate through the entire length of the signal, calculating a probability value for each half hour epoch, where the window increments by half an epoch per iteration (i.e. quarter of an hour). The iteration proceeds until all half-hour epochs have been processed and a vector of probability values for the recording can be obtained.

The overall probability of CS for a single patient/recording may be calculated using the maximum probability found for all epochs classified. The overall performance of the classifier then may be evaluated over the testing set by incorporating a threshold for the decision of CS. This may yield receiver-operating characteristics (ROC) such as the example depicted in FIG. 14.

Figure 14:
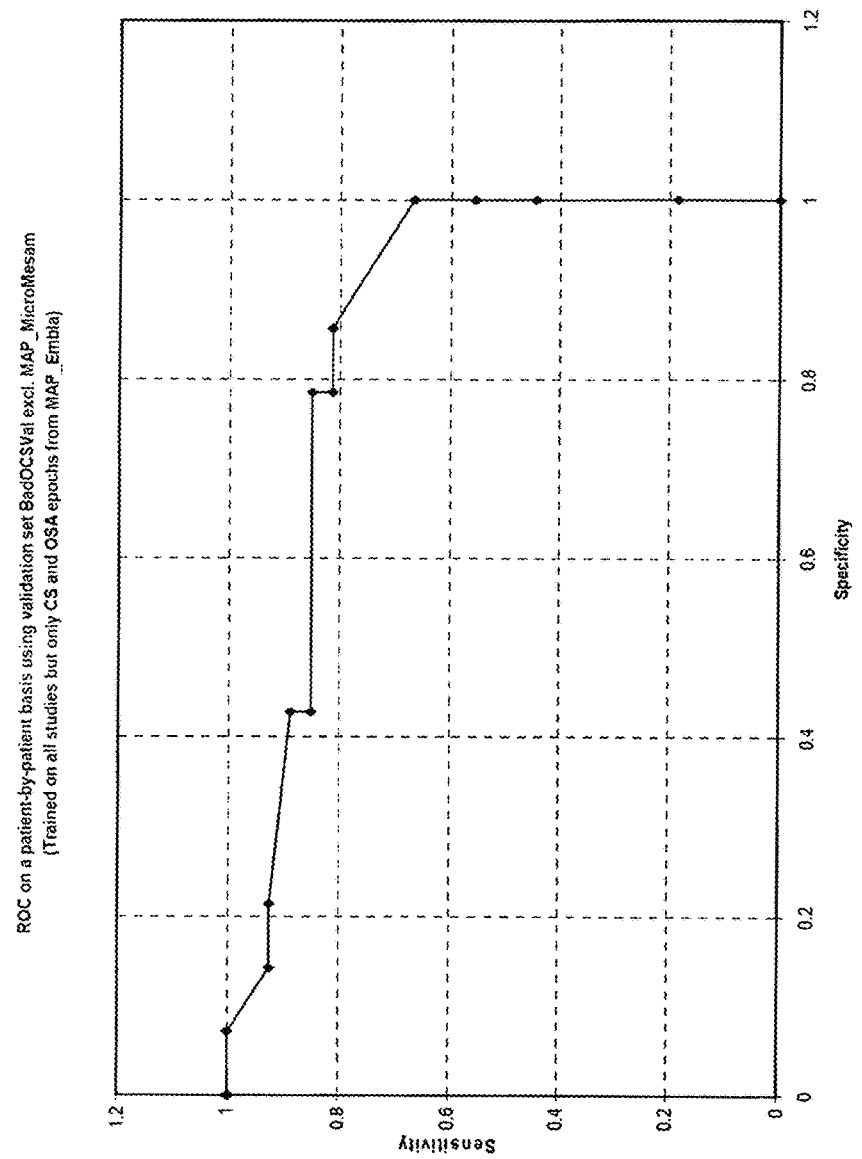
FIG. 14 shows receiver operating characteristics on a patient-by-patient basis.

Each point in FIG. 14 on the ROC curve represents a 0.05 increment/decrement of probability over its adjacent point. The maximum area is achieved at a threshold probability of 0.75 when sensitivity is 0.8148 and specificity is 0.8571. By raising the threshold probability further to 0.8, full specificity can be achieved at the expense of a lower sensitivity of 0.6667. The following table summarizes the key performance measures on a patient-by-patient basis:

| | |
|---|---|
| Threshold chosen (based on max area) | 0.75 |
| Sensitivity | 0.814815 |
| Specificity | 0.857143 |
| Prior probability assumed | 0.004 |
| Positive Predictive Value (PPV) | 0.02069 |
| Negative Predictive Value (NPV) | 0.99883 |
| False Alarm Rate (FAR) | 0.97931 |
| False Reassurance Rate (FRR) | 0.00117 |
| Positive Likelihood Ratio (LR+) | 5.703704 |
| Negative Likelihood Ratio (LR−) | 0.216049 |

Note that this table assumes a prior probability of 0.004 for patients with CS. This estimate is based on a prevalence of 0.01 of Americans with Congestive Heart Failure (CHF) whose age is over 65 years old reported in the Sleep Medicine Reviews (2006) 10, 33-47 by Jean-Louis Pepin et al. Within the CHF population, a prevalence of one-third to one-half is commonly reported in literature on CSR. By taking the prevalence value for CS within the CHF population as 0.4, the prior probability is calculated as 0.01 multiplied by 0.4, which equals 0.004.

The positive likelihood ratio (LR+) indicates that if a patient is classified as CS positive overall, the pre-test probability of that patient truly having CS is boosted by a factor of 5.7 times. Similarly, the negative likelihood (LR−) if a patient is classified as CS negative overall, the pre-test probability of that patient actually having CS is lowered by a factor of 0.22. LR+ and LR− together indicate to the clinician, the strength of a diagnostic test. According to the rating on the qualitative strength of a diagnostic test by Dan Mayer in his book Essential Evidence-Based Medicine, an LR+ and LR− of 6 and 0.2 respectively is considered "very good". Thus, the diagnostic performance of the example classifier on a patient-by-patient basis can be considered close to "very good".

Application

Figure 13:
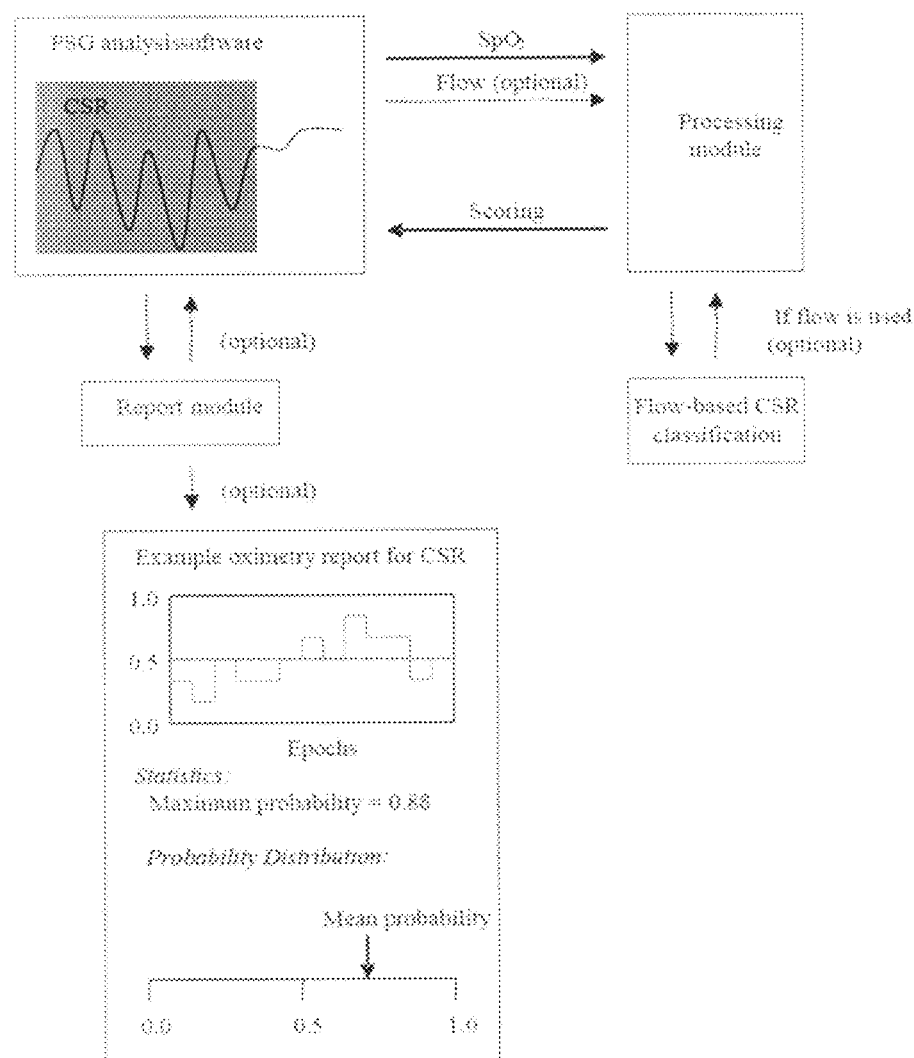
FIG. 13 shows schematically the use of the classifier of the present technology to screen patients for evidence of CSR as a computer-aided diagnostic tool.

One application of such a classifier when implemented by a programmed processor or other processing device is to enable clinicians to screen a large number of patients for evidence of CSR as a computer-aided diagnostic tool. One instance of such application may be used in the environment of home sleep testing, wherein a sleep physician issues a portable SDB screening device such as ApneaLink™ with an oximeter to a patient. Preferably, sleep data may be collected overnight for subsequent analysis by the physician. This analysis by the physician or clinician may be performed offline, that is, after the use of the measuring device in one or more sleep sessions. For example, an algorithm embodying the classifier can be implemented as a module for sleep study analysis software such as Somnologica™ (manufactured by a company called Embla) or ApneaLink™ (manufactured by ResMed Limited). This may allow the automatic scoring of CSR to be marked on an oximetry signal trace or graph. An example embodiment is illustrated in the schematic of FIG. 13. A complementary feature would be a module that automatically generates a report based on the classification results computed by the algorithm. Clinicians would then be able to use the report as a summary to support their decision-making process. Optionally, such a classifier algorithm may be implemented within an SDB screening device to generate data on a display message having a classification of CS as previously discussed.

Furthermore, in some embodiments, the aforementioned oximetry classifier of the present technology may be used or implemented in conjunction with a flow rate classifier, such as the flow rate classifier disclosed in U.S. Patent App. Pub. No. 20080177195, the entire disclosure of which is incorporated herein by reference. For example, in such an embodiment, a controller with one or more programmed processors may include both an oximetry classifier algorithm and a flow rate classifier algorithm. The flow rate classifier may detect the delivered or measured flow rates and then analyze the flow rates with determinant functions and then classify the flow rates based on threshold amounts. A CS probability indicator generated by the controller may then be based on both classifier algorithms, for example, by combining the probability data from each, by using a scheme such as one based on the average of both probabilities or the maximum of either probability as the final conclusion drawn from both classifiers. Such a controller may have increased accuracy and generally better results.

Accordingly, embodiments of the present technology may include a device or apparatus having one or more processors to implement particular CSR detection and/or training methodologies such as the classifiers, thresholds, functions and/or algorithms described in more detail herein. Thus, the device or apparatus may include integrated chips, a memory and/or other control instruction, data or information storage medium. For example, programmed instructions encompassing such detection and/or training methodologies may be coded on integrated chips in the memory of the device or apparatus. Such instructions may also or alternatively be loaded as software or firmware using an appropriate data storage medium. With such a controller or processor, the device can be used for processing data from an oximetry signal. Thus, the processor may control the assessment of a CSR occurrence or probability as described in the embodiments discussed in more detail herein. Moreover, in some embodiments, the device or apparatus itself may optionally be implemented with an oximeter or other blood gas measurement device to measure blood gas itself and then implement the methodologies discussed herein. In some embodiments, the processor control instructions may be contained in a computer readable recording medium as software for use by a general purpose computer so that the general purpose computer may serve as a specific purpose computer according to any of the methodologies discussed herein upon loading the software into the general purpose computer.

Figure 15:
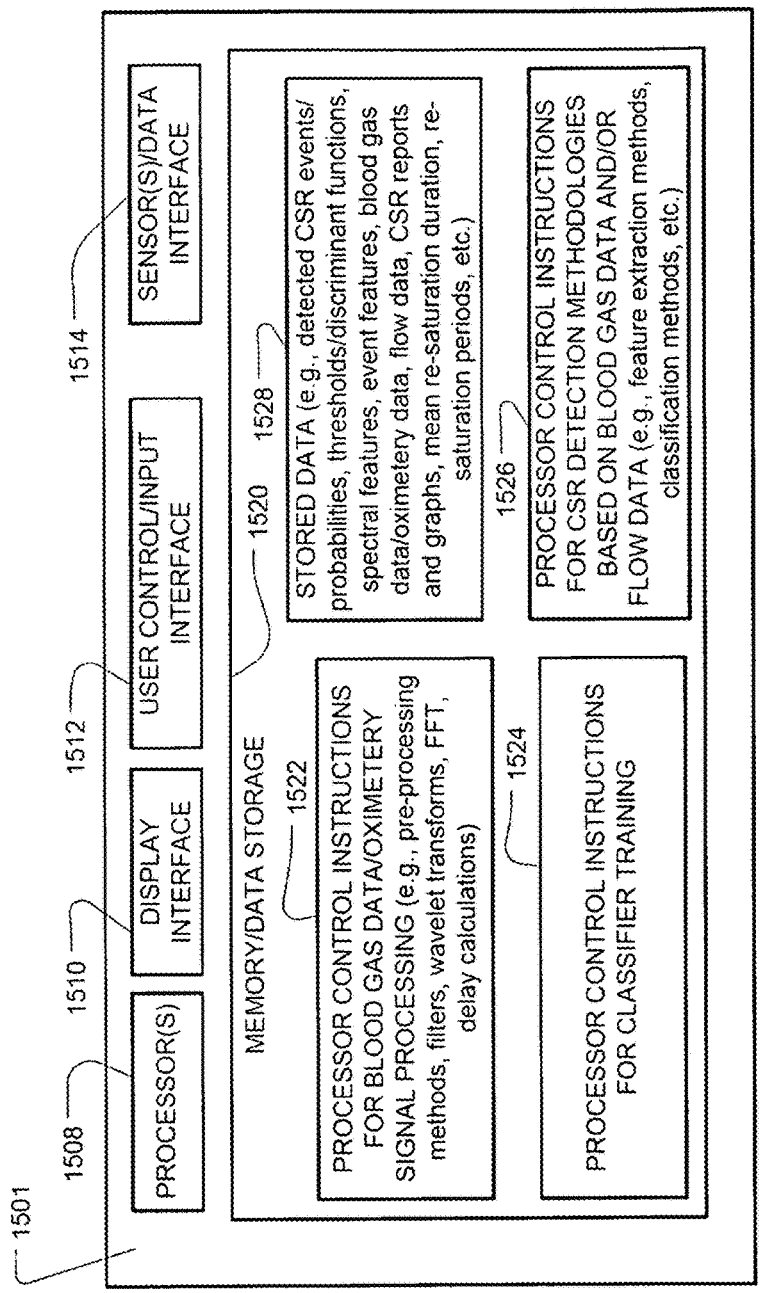
FIG. 15 is a further illustration of components of a CSR detection and/or training system of some embodiments of the present technology.

An example embodiment is illustrated in FIG. 15. In the illustration, the CSR detection device 1501 or general purpose computer may include one or more processors 1508. The device may also include a display interface 1510 to output CS detection reports, results or graphs as described herein such as on a monitor or LCD panel. A user control/input interface 1512, for example, for a keyboard, mouse etc. may also be provided to activate the methodologies described herein. The device may also include a sensor or data interface 1514 for receiving data such as programming instructions, oximetry data, flow data, etc. The device may also typically include a memory/data storage components. These may include processor control instructions for blood gas data/oximetry signal processing (e.g., re-processing methods, filters, wavelet transforms, FFT, delay calculations) at 1522 as discussed in more detail herein. They may also include processor control instructions for classifier training methodologies at 1524. They may also include processor control instructions for CSR detection methodologies based on blood gas data and/or flow data (e.g., feature extraction methods, classification methods, etc.) at 1526. Finally, they may also include stored data 1528 for these methodologies such as detected CSR events/probabilities, thresholds/discriminant functions, spectral features, event features, blood gas data/oximetery data, flow data, CSR reports, mean resaturation duration, resaturation periods, etc.

Figure 16:
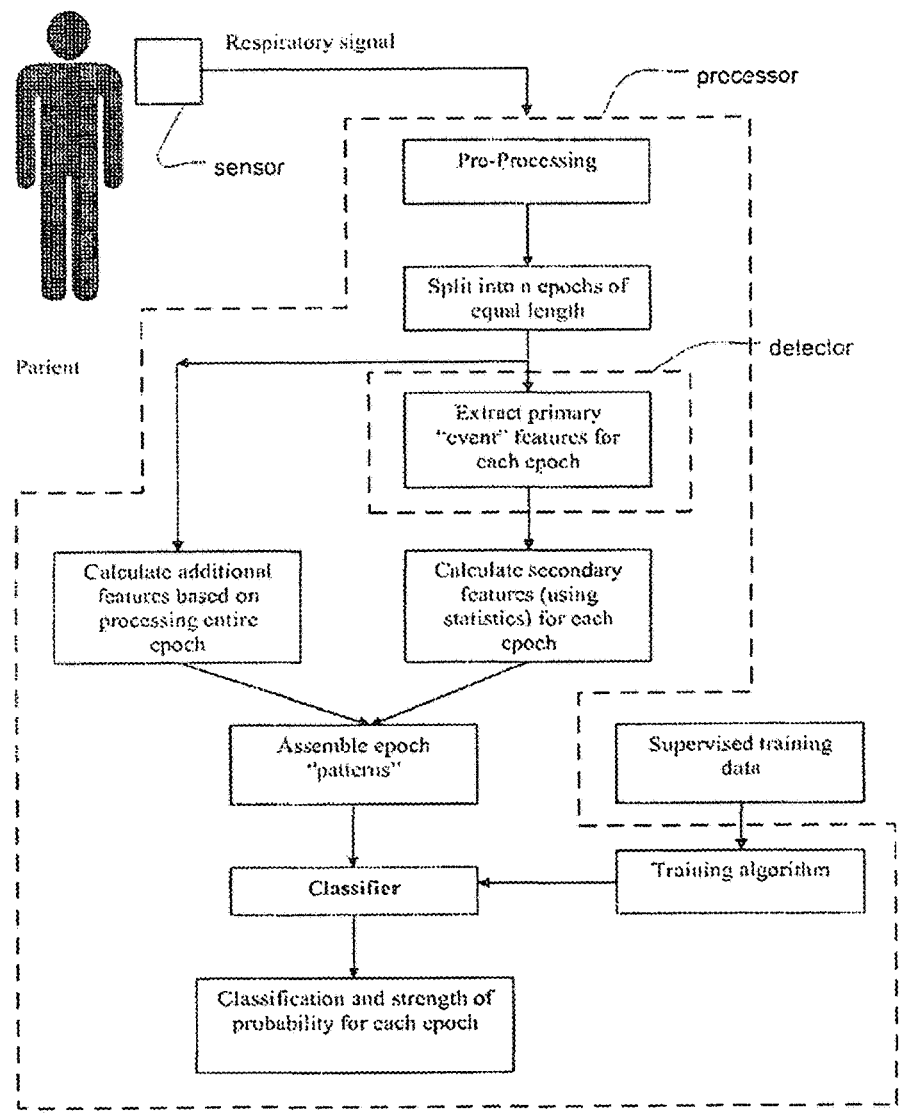
FIG. 16 is a block diagram of the signal processing pathway leading from the patient's respiratory signal through pre-processing, feature extraction based on epochs, through to classification.

FIG. 16 shows one embodiment of the classification process. While the following may be explained in terms of a sequential process, it is understood that the process can be carried out using a non-linear, non-sequential, or non-staged process, or the order of the process may be changed. Also, while FIG. 16 describes an entire process, aspects of the invention may relate to only a subset of that process. A signal representative of respiration is first recorded from a patient using a logging device which includes a data-acquisition system and a memory. The respiratory signal is then processed either on-board by the recording device or off-line using a computer.

Preferably, the signal is initially pre-processed. For example, the signal is filtered to remove unwanted noise and, where appropriate, the baseline is zeroed. The signal may also be linearised depending on the transducer used to detect the respiration.

In the next stage the signal is divided into n epochs of equal length. The epoch length can be as long as the entire record or as short as is practicable to enable detection of respiratory patterns. In one preferred embodiment the epoch length is 30 minutes.

Figure 17:
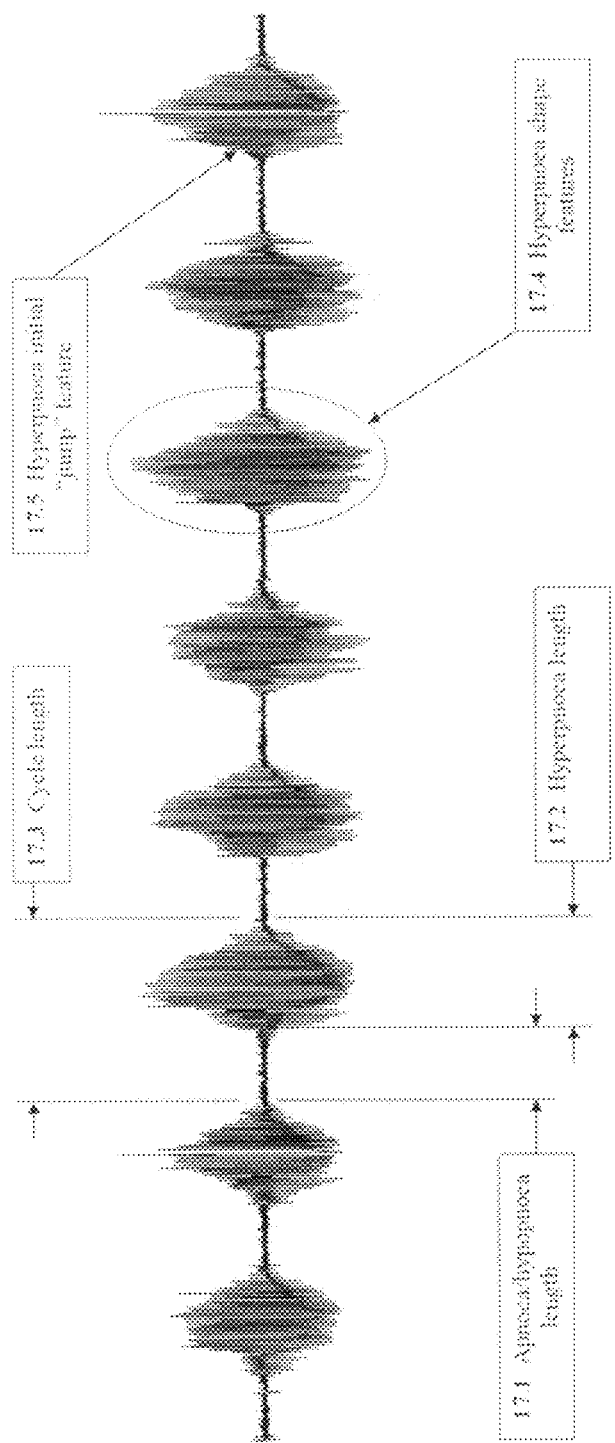
FIG. 17 shows a typical respiratory signal epoch including a number of "events" (in this case apnea-hyperpnoea sequences). Several primary features are either shown explicitly (17.1 apnea/hypopnoea length, 17.2 hyperpnoea length, 17.3 cycle length) or inferred (17.4 shape features of the hyperpnoea, 17.5 a feature representing the initial "jump" at the beginning of the hyperpnoea).

FIG. 17 shows a typical epoch recording in a patient with Cheyne-Stokes breathing. The shape of the curve is reminiscent of the shape of the Sydney Harbor Bridge and is sometimes referred to by that name. See also FIG. 25. The recording consists of eight "events", each event consisting of a hypopnoea (in this case also an apnea) followed by a hyperpnoea. For each event an algorithm is used to detect the beginning and end points such that event lengths can be calculated: e.g., apnea/hypopnoea length and hyperpnoea length. A further algorithm may be used to reject events if they do not follow the correct sequence of hypopnoea/apnea-hyperpnoea. Another further algorithm may be used to reject events that fall outside sensible length scale limits.

Determination of Shape Features

Each hyperpnoea is further processed to derive four so-called "shape features". These features indicate different shaped hyperpnoeas (bell-shaped versus triangle-shaped for example). The shape features are calculated using singular value decomposition of the hyperpnoea ventilation signal as follows: First, the hyperpnoea is extracted from the respiratory signal and the absolute value is taken of the respiratory signal, giving a ventilation signal. The ventilation signal is scaled by its mean value to give a vector of values $V_{hyperp}$. For mathematical convenience the time base of the hyperpnoea [0 . . . T], where T is the end of the hyperpnoea, is mapped to the interval [0 . . . 2π]. A set of four orthogonal functions are calculated and arranged as a 4×m matrix (where m is the number of values in the hyperpnoea signal). A convenient set of orthonormal function are:

$$M_{Basis} = \begin{pmatrix} \frac{1}{\sqrt{\pi}} \sin\left(\frac{t}{2}\right) \\ \frac{1}{\sqrt{\pi}} \cos\left(\frac{t}{2}\right) \\ \frac{\left(3\pi\sin(t) - 8\cos\left(\frac{t}{2}\right)\right)}{\sqrt{\pi(9\pi^2 - 64)}} \\ \frac{\left(3\pi\cos(t) + 4\sin\left(\frac{t}{2}\right)\right)}{\sqrt{\pi(9\pi^2 - 16)}} \end{pmatrix}$$

where t is the time base over the hyperpnoea from 0 to 2π. The basis functions are shown plotted in FIG. 18.1. The four shape features are then calculated as:

$$F_{P(1-4)} = V_{hyperp} \times \text{PseudoInverse}(M_{Basis}),$$

and are normalized by:

$$F_{P(1-4)} = \frac{F_{P(1-4)}}{L_2|F_{P(1-4)}|}$$

where $L_2\|$ is the L2 or Euclidean norm., $$\sqrt{\sum_{i}^{n} x_i^2}$$

The pseudoinverse $M^+$ of a matrix M is a generalization of a matrix inverse, and exists for any (m,n) matrix M (for convenience assume m>n). If such a matrix M has full rank (n) one defines: $M^+ = (M^T M)^{-1} M^T$. The solution of Mx=b is then $x = M^+ b$. (Pseudoinverses are useful because of a general theorem stating that $F = M^+ v$ is the shortest length least squares solution to the problem MF=v.)

Jump Determination

Figure 18:
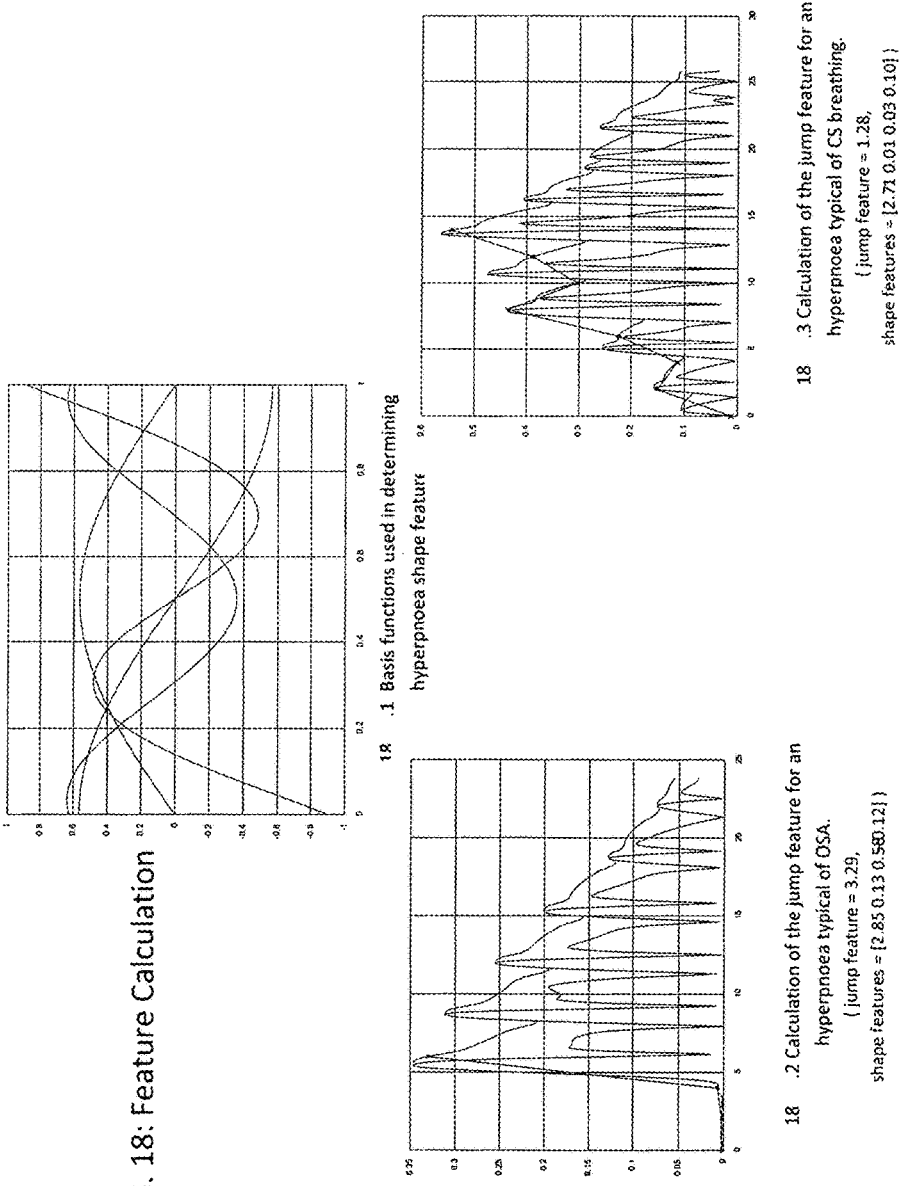
FIG. 18 shows details of the calculation of primary features. 18.1 shows the basis functions used in the determination of the hyperpnoea shape features. 18.2 shows an hyperpnoea typical of OSA together with the calculation of the jump feature displayed graphically. 18.3 shows a similar depiction of an hyperpnoea more typical of CS breathing. In both cases the calculated jump features and shape features are tabled.

Since sudden jumps in the ventilation/flow at the beginning of an hyperpnoea are characteristic of OSA, (see FIG. 17) each hyperpnoea is further processed to derive the so-called "jump" feature, indicative of the extent of any sudden increase in flow, as follows: Again, the hyperpnoea is extracted from the respiratory signal, the absolute value is taken of the respiratory signal, giving a ventilation signal, a droopy peak-detector is used to approximate the envelope of the ventilation signal:

$e[1] = v[1]$ for $i = 2 \ldots m$ if $v[i] \geq e[i-1]$ $e[i] = v[i]$ else $e[i] = e[i-1] + \frac{1}{2.5 f_s}(v[i] - e[i-1])$ end where e[i] is the approximate envelope, $f_s$ is the sampling frequency and v[i] is the ventilation signal. The envelope is interpolated over a new two-second time base (chosen to be roughly the time-length of a breath) to give $e_1$ (between non-breathing intervals). The maximum positive difference $e_1-e_{1(i-1)}$ (over the two second interval) is found in the interpolated signal in the interval between the beginning of the envelope and the point at which the envelope attains its maximum value. Finally, the maximum difference is scaled by the mean value of the ventilation signal to give the "jump feature". FIGS. 18.2 and 18.3 show this process graphically for two representative hyperpnoeas.

Secondary Feature Determination

Secondary features are calculated from primary features using the (measure of variation) statistics detailed below. (Note log denotes the logarithm to base e.) First we define the standard deviation as:

$$STD(F_P) = \sqrt{\frac{1}{n-1}\sum_{i=1}^{n}(F_{Pi} - \overline{F_P})^2},$$

where $$\overline{F_P} = \frac{1}{n}\sum_{i=1}^{n} F_{Pi}$$

For length measures (e.g. hypopnoea length) and the jump feature the four features are:

$$\frac{1}{n}\sum_{i=1}^{n} \log(F_{Pi}) \quad \quad 1.$$

$$\log(STD(\log(F_P))) \quad \quad 2.$$

$$\log\left(\sqrt{\frac{1}{n}\sum_{i=1}^{n}(F_{Pi} - F_{P(i-1)})^2}\right) \text{(To get a normed deviation)} \quad 3.$$

$$\log(STD(F_{Pi} - F_{P(i-1)})) \quad \quad 4.$$

For hyperpnoea shape features the four features are:

$$\frac{1}{n}\sum_{i=1}^{n}(F_{Pi}) \quad \quad 1.$$

$$\log(STD((F_P))) \quad \quad 2.$$

$$\log\left(\sqrt{\frac{1}{n}\sum_{i=1}^{n}(F_{Pi} - F_{P(i-1)})^2}\right) \quad \quad 3.$$

$$\log(STD(F_{Pi} - F_{P(i-1)})) \quad \quad 4.$$

Additional Feature Determination

Additional features can be calculated using the entire (e.g. 30 minute) epoch signal. One such feature is derived from the spectrogram of the epoch signal and determining that Cheyne-Stokes breathing is present if the spectrogram indicates that the signal has a peak. This feature is calculated as follows: First, the mean of the respiratory signal is calculated and subtracted from the respiratory signal and the resulting signal is chopped into n slices which overlap each other by exactly half the slice length. Each slice is next windowed, preferably using a Hanning window (to reduce edge effects).

The use of a Hanning window to prepare the data for a FFT is as follows: The FFT function treats the N samples that it receives as though they formed the basic unit of a repetitive waveform: It assumes that if one took more samples they would repeat exactly, with the (N+1) sample being identical to the first sample, and so on. The usual case is that if one's N samples start at one point in a cycle, they end at some other point, so that if one really did play these back in a loop one would get a discontinuity between the last sample and the first. Hence one tapers both ends of the set of samples down to zero, so they always line up perfectly if looped. The formal name for this process is "windowing", and the "window function" is the shape that we multiply the data by. When the window function is the "raised cosine" 1+cos t the window is termed a Hanning window. Other periodic functions can be used, yielding other windows.

Next, since CS data appears periodic, a fast Fourier transform is applied to each windowed slice, yielding a complex vector result for each slice. The absolute value is taken of each complex result yielding a real valued vector per slice. The mean is taken of the resulting vectors to yield one vector. The natural log is taken of the subsequent vector and the values in the frequency range 0 Hz to 0.075 Hz are extracted to form a sub-vector, which is then de-trended. Cheyne-Stokes behavior is present if the spectrogram indicates the signal has a peak in the range 0 Hz to 0.075 Hz.

Briefly, the method of detrended fluctuation analysis is useful in revealing the extent of long-range correlations in time series, where the time series is a vector of data pairs $(t_i, x_i)$, where t represents time and x represents the variable being measured. De-trending consists of subtracting from the x values, values that have been calculated using a polynomial of order n that has been fitted to the data. For example, for order zero the polynomial is simply the mean of all the x values, and that mean is subtracted from the original values. For order one, the polynomial is simply a linear fit to the data $(t_i, x_i)$. Values calculated using the best linear fit are then subtracted from the original values (so removing any linear "trend"). For order two the fitted polynomial is a quadratic, for order three a cubic etc.

The feature is then calculated as the maximum minus the mean of the de-trended vector. Alternatively one could calculate the entropy of the FFT instead of its peak.

Additional features can be derived by applying wavelet analysis to each epoch. In this case wavelet coefficients or statistics derived from wavelet coefficients are used as features for the epoch. This yields the location of the peak in time. In wavelet analysis a wave packet, of finite duration and with a specific frequency, is used as a window function for an analysis of variance. This "wavelet" has the advantage of incorporating a wave of a certain period, as well as being finite in extent. A suitable wavelet (called the Morlet wavelet) is a sine wave multiplied by a Gaussian envelope.

Classification

A subset of features is then selected for use by the classifier. It is known that a particular subset of features can provide more accurate classification than the full set of features. This is caused in part by the so-called "curse of dimensionality", whereby the required number of training samples increases with the number of features used. The curse of dimensionality causes networks with lots of irrelevant inputs to behave relatively badly: Where the dimension of the input space is high, the network uses almost all its resources to represent irrelevant portions of the space.

An algorithm is employed to select the best subset based on the training data. Ideally every subset of features should be tested for accuracy and the best subset chosen. The number of subsets is $2^n-1$ where n is the number of features. Unless there is a small number of features the exploration of all subsets is impractical and, in any case, accuracy measures tend to be noisy which further hampers the search for the best subset. Alternative algorithms that enable selection of "good" feature subsets include "best first", "remove worst", "random start with add and remove", "simulated annealing" and genetic algorithms.

A method often used to measure accuracy is 10-fold cross-validation. The training data are split into ten groups or folds and ten different accuracy tests are performed. In each case 9 tenths of the folds are used for training and the resulting classifier is tested for accuracy on the remaining tenth. Statistics are performed on the 10 results to give a measure of accuracy.

Training the Classifier

Once a feature subset is chosen, the classifier is trained using the entire training data set. A number of classifier types are available including: Baysean maximum likelihood linear and quadratic discriminants, neural networks and support vector machines. In each case a discriminant function is calculated which, when applied to features calculated from new data to be classified, provides probability estimates for different classes. The data (epoch) is assigned to the class with the highest probability.

In one particular embodiment the discriminant function includes or preferably consists of two weight vectors (of the same length as the feature subset) and two constants. When the desired feature subset has been extracted from the respiratory epoch, the discriminant functions and probability are calculated as follows:

$$d_1 = W_1 \Box F + C_1$$

$$d_2 = W_2 \Box F + C_2$$

$$\text{probability} = \frac{e^{(d1-d2)}}{1 + e^{(d1-d2)}}$$

where $W_1$, $W_2$ are vectors and $C_1$, $C_2$ are constants.

The probability cutoff may be set at 0.5 in which case a probability of 1.0 would equate to class A and a probability of 0.0 to class B. The cutoff can be adjusted to suit the desired sensitivity and specificity. This is a two-way classification. With suitable training data, a three-way classification is also possible as are even higher n-way classifications.

Figure 19:
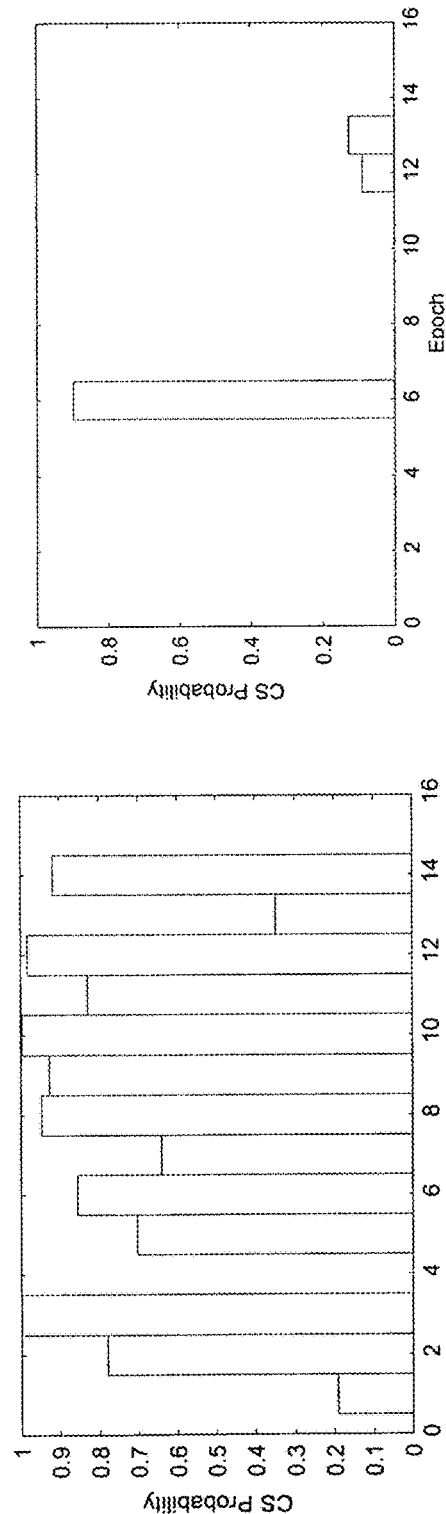
FIG. 19 shows examples of epoch classification, e.g., using bar charts.

In one particular embodiment the classification of each epoch could be displayed in a bar chart as in FIG. 19. Frame 19.1 shows a bar chart where many epochs show a high probability of a class of respiration (in this case CS-like breathing). This provides an "at-a-glance" indication of a patient record. Frame 19.2 shows a bar chart where only a single epoch displays strong CS-like tendency. This provides an indication of where in the patient's record a more detailed investigation is warranted.

Cheyne-Stokes Classifier Based on a Flow Signal or an Spo2 Signal or Both

The ApneaLink device is capable of measuring an estimate of a patient's flow signal which can be used as an input to the algorithm described herein. Equally there are similar portable devices that can measure and log SpO2, the saturation of oxyhemoglobin in the blood as estimated by pulse oximetry. Pulse oximetry is a simple non-invasive method of monitoring the percentage of haemoglobin (Hb) which is saturated with oxygen. The pulse oximeter consists of a probe attached to the patient's finger or ear lobe which is linked to a computerised unit.

SpO2 is typically reported as a percentage, values above 95% being normal and those below 95% indicating some degree of hypoxia (lack of oxygen in the blood). Should a patient undergo an apnoea or hypopnoea, it is usual for the SpO2 signal to fall concomitantly with the ventilation, albeit after some delay. During Cheyne-Stokes breathing the SpO2 signal will undergo the classic waxing and waning pattern also characteristic of the ventilation.

Hence, it is conceivable that the algorithm described herein might use a flow signal estimate (ventilation) or an SpO2 signal or both signals to classify breathing patterns as being typical of Cheyne-Stokes, OSA, mixed apnoeas etc.

Figure 27:
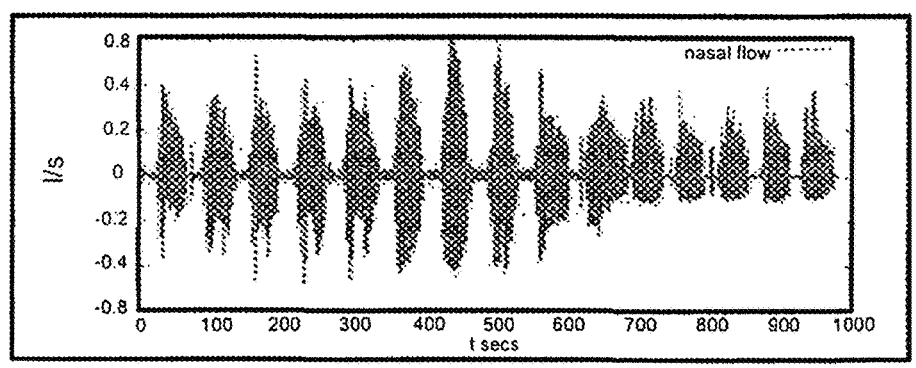
FIG. 27 shows a Cheyne-Stokes patient's nasal flow signal over about 15 minutes.
Figure 28:
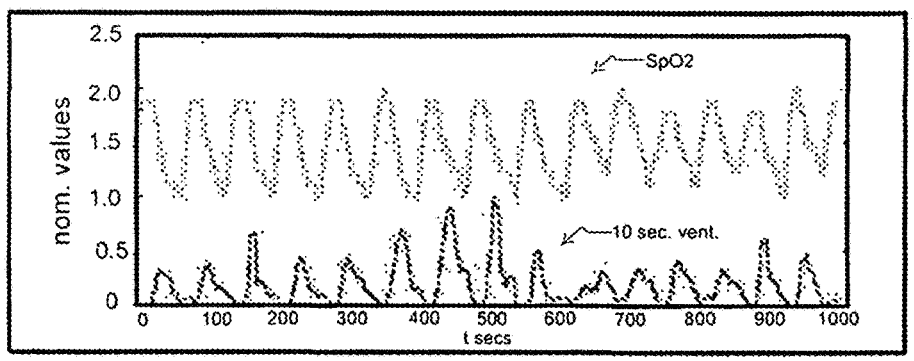
FIG. 28 shows a patient's Spo2 signal (saturation) and ventilation signal (low-pass filtered absolute value of flow).

FIG. 27 shows a Cheyne-Stokes patient's nasal flow signal over about 15 minutes. FIG. 28 shows the same patient's Spo2 signal (saturation) and ventilation signal (low-pass filtered absolute value of flow). The signals have been normalized and shifted to display them n the same graph. The same pattern recognition techniques may be applied to both signals. For example: segment the signal into hypopnoeas/hyperpnoeas; analyze the shape of the hypopnoeas; determine the cycle lengths and space ratios; perform a spectrogram (average of absolute value of a number of FFTs); determine peaks in the spectrogram at the CS frequency; determine a morphologic feature in both signals such as the jump feature; perform a continuous wavelet transform on both signals and use ridge finding techniques t follow any CS frequency component over time.

EXAMPLE 1

A set of data for testing the ability of flow data to be classified into OSA and CS instances consisted of 90 patient studies of approximately 8 hours each. For purposes of the test, both nasal pressure, flow and two effort signals (abdomen & thorax) were recorded, making a confirming diagnosis of the underlying disease possible. The set was divided into 3 groups of 30 patients: OSA (obstructive apnoea), CS and Mixed. The data were further classified (initially) on a 30-minute time-bin basis. The time periods were classified into the following categories: No apnoeas or hypopnoeas (<5) within the time period; Primarily CS breathing (>90%); Primarily OSA (>90%); Primarily (>90%) apnoeas and hypopnoeas of mixed type (i.e. having a central component followed by a number of obstructed breaths); A combination of different events, typically brief periods of CS or mixed apnoeas interspersed between OSA; Patient is moving and the signal is of too low a quality to be useable.

Typically if CS disease is present, CS breathing will occur in large blocks of at least 20-30 minutes. The data set contained very few periods of "pure" mixed apnoeas. Rather, the mixed group of 30 patients contained periods of OSA, CS breathing or a mixed picture.

Feature Analysis

Figure 20:
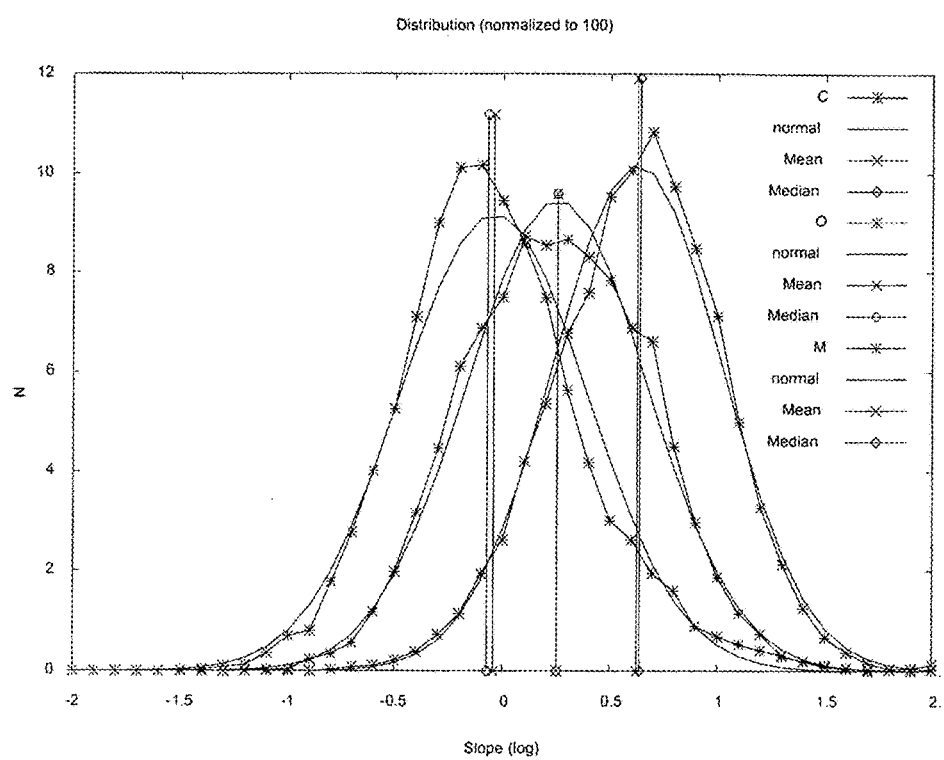
FIG. 20 shows the distribution of the normalized max jump in a hyperpnoea signal.

All features were analyzed by calculating distributions for the different groups (OSA, Mixed, and CS). The distribution was normalized by application of an appropriate function, for example FIG. 20 shows the distribution of the normalized max jump in hyperpnoea signal between beginning of hyperpnoea and time of peak flow after application of log-to-base-e. The leftmost curves represent a "normal" or Gaussian distribution. It can be seen that the application of the log function has normalized the distributions and, further, that this feature shows good separation between the CS (left) and OSA (rightmost) groups.

Cluster Analysis

Figure 21:
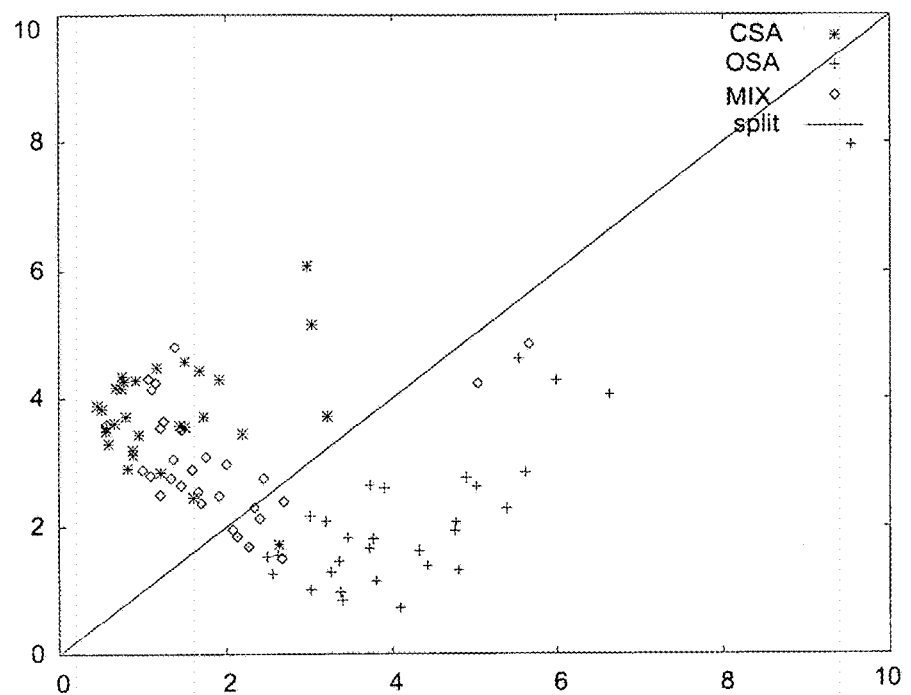
FIG. 21 shows a cluster analysis of CS and OSA patients.

Both k-means and fuzzy k-means clustering techniques were utilized to visualize feature separation power. The features were first averaged on a per-patient basis and then cluster analysis was used to demonstrate a natural clustering into correct groups. FIG. 21 shows such an analysis. The Euclidean 2-norm distance from each of two cluster centers is plotted one against the other. The CS and OSA patients naturally fall into two groups except for one CS patient. The Mixed patients fall into one group or the other depending on the length of time spent during the night in different breathing patterns. The separating diagonal in the figure represents a naive classifier suitable for per-patient grouping. What such a classifier cannot do is find a short period of CS breathing from amongst an otherwise OSA-dominated night.

Feature Temporal Averaging

The training of a classifier using patterns assigned to individual events is problematical. Temporal averaging was used to reduce the amount of calculation, while also (potentially) increasing statistical power. A 30-minute time-bin was chosen as a best first-guess. After temporal averaging, a new set of per-time-bin patterns is created. The raw features used (visible separation of groups) were: hypopnoea length; hyperpnoea length; $1^{st}$ Fourier shape feature; $2^{nd}$ Fourier shape feature; and normalized max jump. The time-averaged 30-minute bin features tested were (std=standard deviation, meansq=mean of square of values, sqrt=square root, shift=allows calculation of temporal difference).

Classifier Training and Testing

Once the data had been processed and the "expert" diagnosis made, a group of 1440 30-minute bins was available for classifier training (90 patients×16 bins).

Classifier Selection

Numerous statistical methods exist for the training of a classifier from n-dimensional data, e.g.: nearest neighbor, neural nets, cluster analysis. However, because the data "appeared" linearly separable, Bayesian decision theory was used. This theory (which relies on underlying normal probability density functions) uses the minimization of the Bayes error to calculate a discriminant surface. Such a surface separates the data into one of n categories (in this case 2). Both linear and quadratic discriminant functions were utilized. The former separates the data with a hyperplane in m dimensions (where m is the number of features) while the latter separates the data with a hyperquadric. A hyperplane discriminant is always preferred (assuming accuracy of the same order), as it will tend to be well behaved in areas of minimal data coverage.

Over-Optimistic Train and Test

Figure 22:
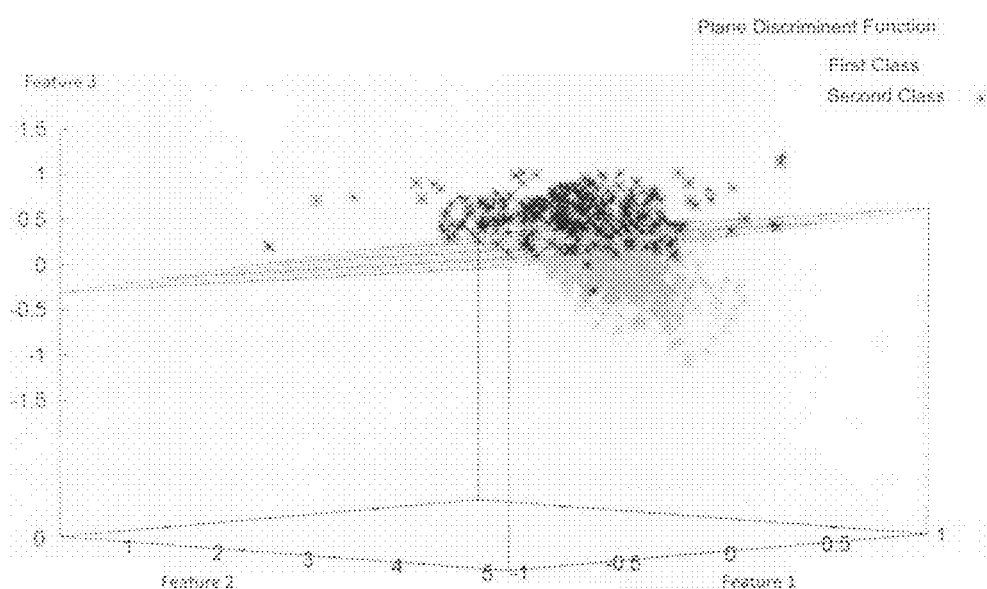
FIG. 22 shows results from a LD (linear) classifier.
Figure 23:
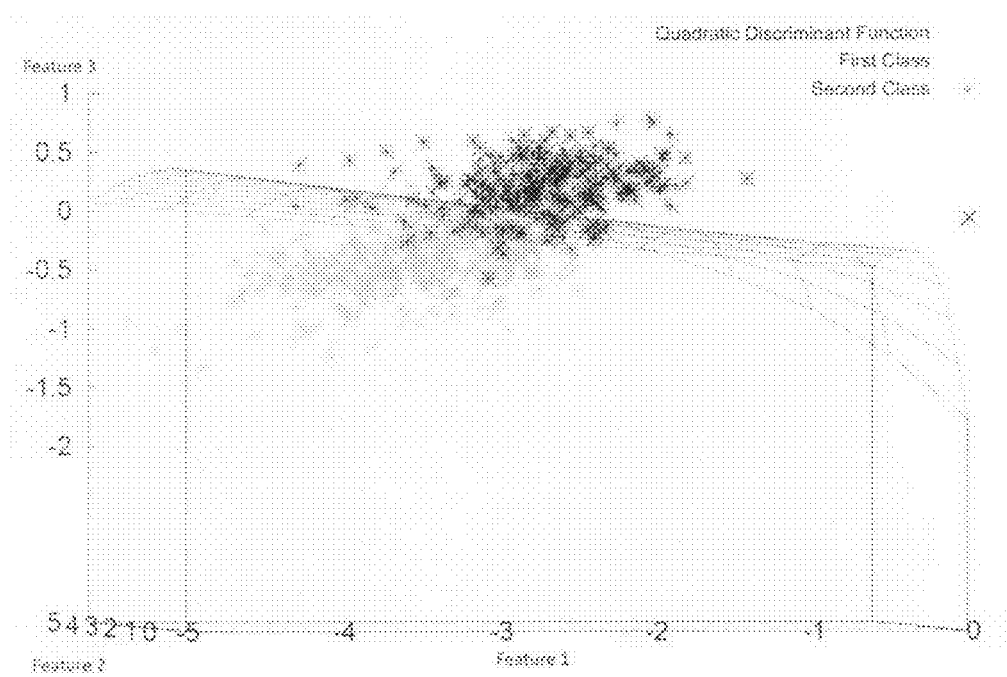
FIG. 23 shows results from a QD (quadratic) classifier.
Figure 24:
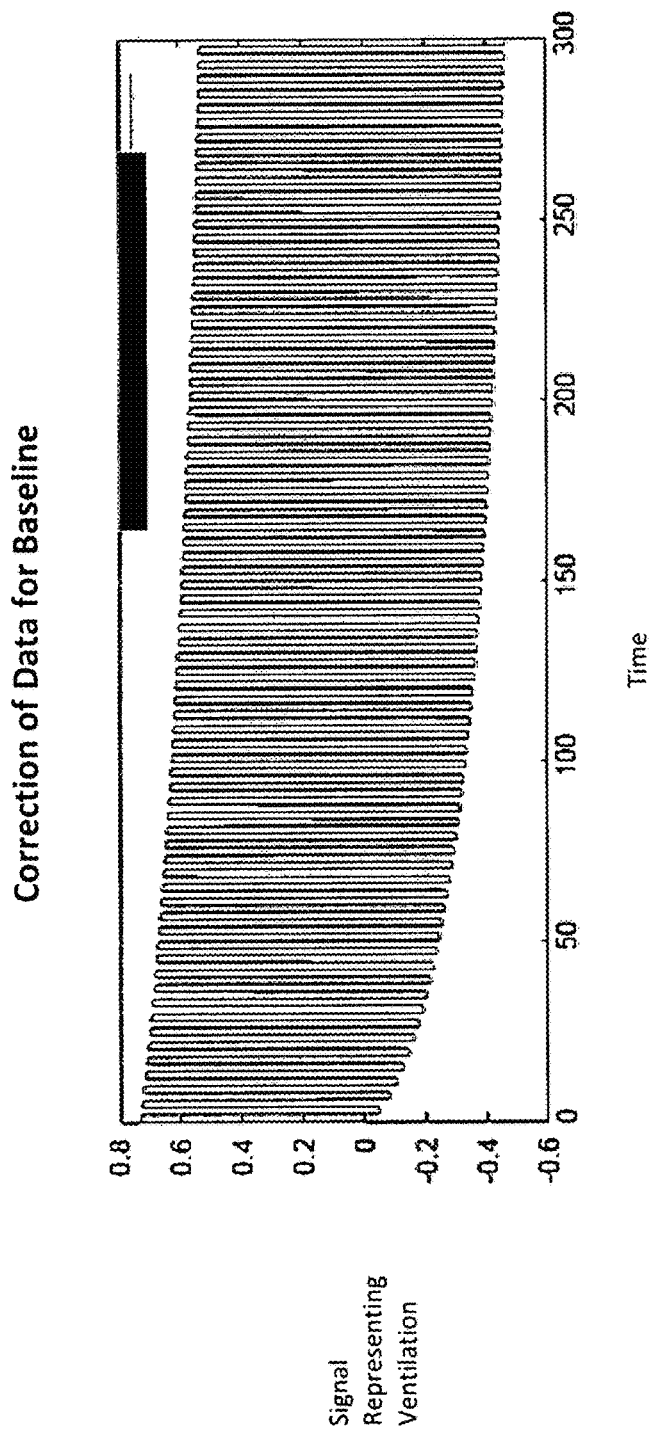
FIG. 24 shows the correction of data for baseline offset.

The classifier was trained using the training set and then the classifier was tested using the same data. This results in over-optimistic values of sensitivity and specificity, as one would intuitively expect. However, again this is an insightful process and one can use a minimal features set (.ltoreq.3 features) in order to visualize the result. FIG. 22 shows an LD classifier (plane shows equi-probability surface). FIG. 23 shows a QD classifier (quadric shows equi-probability surface).

Results

During each test the accuracy, sensitivity and specificity were noted as was the current features set (or group of feature sets) with the best accuracy. Estimates of accuracy, sensitivity and specificity resulted of the order of 91%, 91% and 96% respectively.

EXAMPLE 2

Flow Filtering

The flow is filtered first to remove unwanted and uninteresting high-frequency content. The filter used is a digital FIR (finite impulse response) filter designed using the Fourier method using a rectangular window. The filter has a pass-band from 0 to 0.9 Hz, a transition band from 0.9 to 1.1 Hz and a stop band above 1.1 Hz. The number of terms in the filter varies with sampling frequency. The flow signal is filtered by convolving the time series point-wise with a filter vector.

Ventilation Calculation

Figure 25:
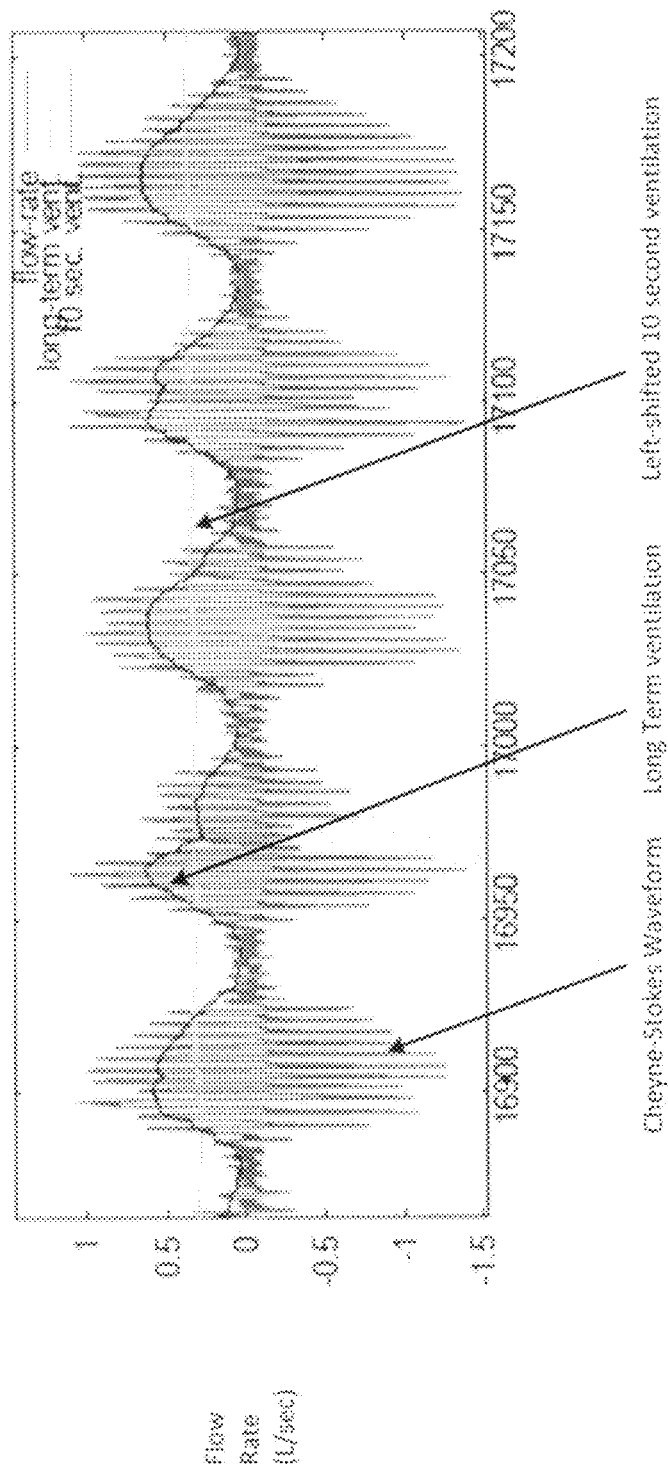
FIG. 25 shows a Cheyne-Stokes flow waveform, the long-term ventilation and the left-shifted 10-second ventilation for a typical patient.

A long-term ventilation signal $y_{long}$ is calculated using a simple (first order) low-pass filter applied to the flow signal. A time constant of 200 seconds is used (longer than the longest possible cycle of Cheyne-Stokes breathing). In order to measure ventilation (and not mean flow), the filter is applied to the square of the flow signal and the square root is taken of the filter output. Next, a ten-second ventilation $y_{10}$ is calculated (a more "recent" measure). This measure is created by convolving the square of the flow signal with a 10-second square wave with an area of one, i.e. a 10-second-long moving average, and then taking the square-root of the result. This filter will have a five second delay constant over the frequency range of interest. For this reason the signal is shifted left by five seconds so that it "lines up" with the original signal for timing purposes. FIG. 25 shows a Cheyne-Stokes flow waveform (large amplitude rapid varying curve), the long-term ventilation (low amplitude slowly varying curve) and the left-shifted 10-second ventilation (moderately varying curve) for a typical patient.

Event Detection from Ventilation Signals

The 10-second ventilation signal is used to create low and high thresholds for detection of events (hypopnoea-hyperpnoea sequences). The thresholds are:

$thresh_{low}=0.5 \times y_{long}$;
$thresh_{high}=0.75 \times y_{long}$;

The timing of events is calculated using the following algorithm:

1. Find all points where $y_{10} < thresh_{low}$.
2. Find all contiguous sections of the above points. These are provisional hypopnoeas.
3. Find all points where $y_{10} > thresh_{high}$.
4. Iterate over all of the hypopnoeas identified in step 2. If no points identified in step 3 (hyperpnoeas) fall between hypopnoea n and hypopnoea n+1, then the hypopnoeas n & n+1 are joined together (because no hyperpnoea has been identified between them) to form one hypopnoea. Repeat for all iterations.

5. The hypopnoeas are now confirmed. All inter-hypopnoea regions are considered hyperpnoeas. Each hypopnoea-hyperpnoea "event" constitutes one possible Cheyne-Stokes cycle. E.g. in FIG. 25 there are five cycles shown.
Calculate Event Timings Event timings are calculated for each event as follows:

$\tau_{hypopnoea}$=(end_of_hypopnoea)–t (beginning_of_ hypopnoea);

$\tau_{cycle}$=t (beginning_of_next_hypopnoea)–t (beginning_of_hypopnoea);

$\tau_{hyperpnoea}$=$t_{cycle}$–$t_{hypopnoea}$;

Obviously the above events will include some unwanted "garbage". For example, a one-hour-long period of normal breathing bracketed on each side by Cheyne-Stokes breathing will look like a one-hour-long hyperpnoea! ($y_{10}$ always greater than threshold). Hence, the following sensible limits are applied to the events:

$\tau_{hypopnoea}$: minimum=10 seconds, maximum=100 seconds, $\tau_{cycle}$: minimum=15 seconds, maximum=250 seconds, $\tau_{hyperpnoea}$: minimum=5 seconds.

Figure 26:
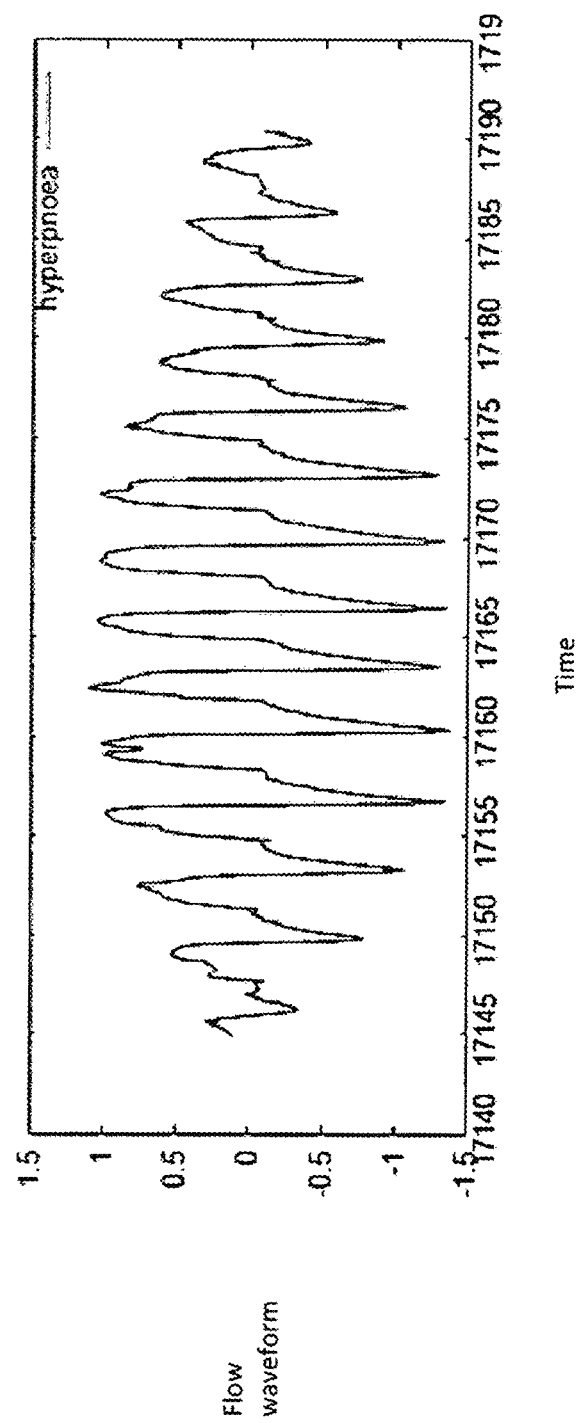
FIG. 26 depicts those parts of the flow waveform that correspond to hyperpnoeas.

All events outside these limits are rejected and not processed. We now have event timings and the ability to extract parts of the flow waveform for further analysis. For example, we can iterate over all the events and select out those parts of the flow waveform that correspond to hyperpnoeas. FIG. 26 is an example where we have selected out an hyperpnoea from the above sequence and plotted it separately. In all further processing it is the 1 Hz filtered flow signal that is used for feature extraction.

While the technology has been described in connection with what are presently considered to be practical and preferred embodiments, it is to be understood that the technology is not to be limited to the disclosed embodiments, but on the contrary, is intended to cover various modifications and equivalent arrangements included within the spirit and scope of the technology.

The invention claimed is:

1. A computer implemented method of detecting an occurrence of Cheyne-Stokes respiration in one or more programmed processors comprising:
    accessing blood gas data representing a measured blood gas signal from an oximeter;
    determining a duration of one or more contiguous periods of changing saturation of a blood gas from the blood gas data;
    determining a presence of a peak in a predetermined frequency range for de-saturation and re-saturation cycles of the blood gas data;
    detecting the occurrence of Cheyne-Stokes respiration from (a) a comparison of the determined duration and a threshold derived to differentiate saturation changes due to Cheyne-Stokes respiration and saturation changes due to obstructive sleep apnea, and (b) a comparison of the determined peak to a further threshold;
    generating an output indicating the detected occurrence of Cheyne-Stokes respiration; and
    determining a quality indicator for determining a confidence level associated with detecting the occurrence of Cheyne-Stokes respiration,
    wherein the processor determines the quality indicator by determining a number of samples where the measured blood gas signal drops below a predetermined percentage threshold.

2. The method of claim 1 wherein the one or more contiguous periods of changing saturation comprises re-saturation periods and the measured blood gas signal comprises an oximetry signal.

3. The method of claim 2 wherein the determined duration comprises a mean period length and wherein the detecting indicates an occurrence when the mean period length exceeds the threshold.

4. The method of claim 3 wherein the threshold comprises a discriminant function.

5. The method of claim 4 wherein the detecting the occurrence further comprises determining a distance from the threshold and comparing the distance to a further threshold.

6. The method of claim 1 further comprising processing the blood gas data to remove artifact data.

7. The method of claim 1 further comprising measuring the blood gas with the oximeter.

8. The method of claim 1, wherein the predetermined percentage threshold is 10%.

9. The method of claim 1, wherein the quality indicator is a function of a ratio of the number of samples where the measured blood gas signal drops below the predetermined percentage threshold and a total number of samples considered.

10. A computer implemented method of detecting an occurrence of Cheyne-Stokes respiration in one or more programmed processors comprising:
    accessing blood gas data representing a measured blood gas signal from an oximeter;
    determining a duration of one or more contiguous periods of changing saturation of a blood gas from the blood gas data;
    determining a presence of a peak in a predetermined frequency range for de-saturation and re-saturation cycles of the blood gas data;
    detecting the occurrence of Cheyne-Stokes respiration from (a) a comparison of the determined duration and a threshold derived to differentiate saturation changes due to Cheyne-Stokes respiration and saturation changes due to obstructive sleep apnea, and (b) a comparison of the determined peak to a further threshold;
    generating an output indicating the detected occurrence of Cheyne-Stokes respiration; and
    processing the blood gas data to remove artifact data,
    wherein the processing the blood gas data to remove artifact data comprises determining in the one or more programmed processors a beginning and end of a motion artifact period in the blood gas data by identifying with a derivative signal of the blood gas data an initial negative spike with a first lesser threshold followed by a positive spike with a second greater threshold.

11. The method of claim 10, further comprising determining a quality indicator for determining a confidence level associated with detecting the occurrence of Cheyne-Stokes respiration.

12. The method of claim 11, wherein the processor determines the quality indicator by determining a number of samples where the measured blood gas signal drops below a predetermined percentage threshold.

13. An apparatus to detect an occurrence of Cheyne-Stokes breathing, the apparatus comprising:
    a memory for blood gas data representing a measured blood gas signal from an oximeter; and a processor coupled with the memory, the processor being configured (a) to determine a duration of one or more contiguous periods of changing saturation of a blood gas from the blood gas data; (b) to determine a presence of a peak in a predetermined frequency range for de-saturation and re-saturation cycles of the blood gas data; (c) to detect an occurrence of Cheyne-Stokes respiration from (1) a comparison of the determined duration and a threshold derived to differentiate saturation changes due to Cheyne-Stokes respiration and saturation changes due to obstructive sleep apnea, and (2) a comparison of the determined peak to a further threshold; and (d) to generate an output indicating the detected occurrence of Cheyne-Stokes respiration, wherein the processor is further configured to determine a quality indicator for determining a confidence level associated with detecting the occurrence of Cheyne-Stokes respiration, and wherein the processor determines the quality indicator by determining a number of samples where the measured blood gas signal drops below a predetermined percentage threshold.

14. The apparatus of claim 13 wherein the one or more contiguous periods of changing saturation comprises re-saturation periods and the measured blood gas signal comprises an oximetery signal.

15. The apparatus of claim 14 wherein the determined duration comprises a mean period length and wherein the detecting indicates an occurrence when the mean period length exceeds the threshold.

16. The apparatus of claim 15 wherein the threshold comprises a discriminant function.

17. The apparatus of claim 16 wherein the processor is configured to detect the occurrence by further determining a distance from the discriminant function and comparing the distance to a further threshold.

18. The apparatus of claim 13 wherein the processor is further configured to process the blood gas data to remove artifact data.

19. The apparatus of claim 13 further comprising the oximeter, coupled with the processor, to generate the blood gas signal.

20. The apparatus of claim 13, wherein the predetermined percentage threshold is 10%.

21. The apparatus of claim 13, wherein the quality indicator is a function of a ratio of the number of samples where the measured blood gas signal drops below the predetermined percentage threshold and a total number of samples considered.

22. An apparatus to detect an occurrence of Cheyne-Stokes breathing, the apparatus comprising:
a memory for blood gas data representing a measured blood gas signal from an oximeter, and
a processor coupled with the memory, the processor being configured (a) to determine a duration of one or more contiguous periods of changing saturation of a blood gas from the blood gas data; (b) to determine a presence of a peak in a predetermined frequency range for de-saturation and re-saturation cycles of the blood gas data; (c) to detect an occurrence of Cheyne-Stokes respiration from (1) a comparison of the determined duration and a threshold derived to differentiate saturation changes due to Cheyne-Stokes respiration and saturation changes due to obstructive sleep apnea, and (2) a comparison of the determined peak to a further threshold; and (d) to generate an output indicating the detected occurrence of Cheyne-Stokes respiration, wherein the processor is further configured to process the blood gas data to remove artifact data, and wherein the processor is configured to process the blood gas data to remove artifact by determining a beginning and end of a motion artifact period in the blood gas data by identifying with a derivative signal of the blood gas data an initial negative spike with a first lesser threshold followed by a positive spike with a second greater threshold.

23. The apparatus of claim 22, wherein the processor is further configured to determine a quality indicator for determining a confidence level associated with detecting the occurrence of Cheyne-Stokes respiration.

24. The apparatus of claim 23, wherein the processor determines the quality indicator by determining a number of samples where the measured blood gas signal drops below a predetermined percentage threshold.

25. An apparatus for detecting an occurrence of Cheyne-Stokes respiration comprising:
means for accessing blood gas data representing a measured blood gas signal from an oximeter;
means for determining a duration of one or more contiguous periods of changing saturation of a blood gas from the blood gas data;
means for determining a presence of a peak in a predetermined frequency range for de-saturation and re-saturation cycles of the blood gas data; and
means for detecting the occurrence of Cheyne-Stokes respiration from (a) a comparison of the determined duration and a threshold derived to differentiate saturation changes due to Cheyne-Stokes respiration and saturation changes due to obstructive sleep apnea, and (b) a comparison of the determined peak to a further threshold; and
means for generating an output indicating the detected occurrence of Cheyne-Stokes respiration
means for determining a quality indicator for determining a confidence level associated with detecting the occurrence of Cheyne-Stokes respiration, wherein the quality indicator is determined by determining a number of samples where the measured blood gas signal drops below a predetermined percentage threshold.

* * * * *